(12) United States Patent
Demarais

(10) Patent No.: US 8,057,384 B2
(45) Date of Patent: Nov. 15, 2011

(54) METHODS AND DEVICES FOR REDUCING HOLLOW ORGAN VOLUME

(75) Inventor: Denise M. Demarais, Los Gatos, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 140 days.

(21) Appl. No.: 12/030,103

(22) Filed: Feb. 12, 2008

(65) Prior Publication Data

US 2008/0132925 A1 Jun. 5, 2008

Related U.S. Application Data

(62) Division of application No. 11/067,598, filed on Feb. 25, 2005, now Pat. No. 7,708,684.

(60) Provisional application No. 60/547,961, filed on Feb. 27, 2004.

(51) Int. Cl.
    *A61F 2/00* (2006.01)
(52) U.S. Cl. .......................................... 600/37; 606/153
(58) Field of Classification Search ................. 606/151, 606/153, 157, 216; 24/20 R, 21, 20 CW, 24/20 TT, 16 PB, 30.5 R, 30.5 W, 30.5 S; 600/37
    See application file for complete search history.

(56) References Cited

U.S. PATENT DOCUMENTS

| 2,108,206 | A | 2/1938 | Meeker |
|---|---|---|---|
| 2,508,690 | A | 7/1948 | Schmerl |
| 3,372,443 | A | 3/1968 | Daddona, Jr. |
| 3,395,710 | A | 8/1968 | Stratton et al. |
| 3,986,493 | A | 10/1976 | Hendren, III |
| 4,057,065 | A | 11/1977 | Thow |
| 4,063,561 | A | 12/1977 | McKenna |
| 4,133,315 | A | 1/1979 | Berman et al. |
| 4,134,405 | A | 1/1979 | Smit |
| 4,198,982 | A | 4/1980 | Fortner et al. |
| 4,246,893 | A | 1/1981 | Berson |
| 4,258,705 | A | 3/1981 | Sorensen et al. |
| 4,311,146 | A | 1/1982 | Wonder |
| 4,315,509 | A | 2/1982 | Smit |
| 4,343,066 | A | 8/1982 | Lance |
| 4,402,445 | A | 9/1983 | Green |
| 4,416,267 | A | 11/1983 | Garren et al. |

(Continued)

FOREIGN PATENT DOCUMENTS

EP 0 137 878 A1 4/1985

(Continued)

OTHER PUBLICATIONS

Benjamin, S.B., et al., *A Double-Blind Cross Over Study of the Garren-Edwards anti-Obesity Bubble* Abstract Submitted to A/S/ G/E/ 1987, Georgetown University Hospital and Fairfax Hospital, Washington, D.C. and Fairfax, VA.

(Continued)

*Primary Examiner* — Kevin T Truong
(74) *Attorney, Agent, or Firm* — Nutter McClennen & Fish LLP

(57) ABSTRACT

Methods and devices for providing a minimally-invasive placement of a mechanical structure for reducing the volume of a hollow body organ. Intragastric bands may be secured within the hollow body organ and then reduced in diameter to form a stricture within the hollow body organ. The strictures may be placed anywhere within the hollow body organ, and more than one stricture may be formed within the hollow body organ.

8 Claims, 14 Drawing Sheets

U.S. PATENT DOCUMENTS

| | | |
|---|---|---|
| 4,458,681 A | 7/1984 | Hopkins |
| 4,485,805 A | 12/1984 | Foster, Jr. |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,694,827 A | 9/1987 | Weiner et al. |
| 4,696,288 A | 9/1987 | Kuzmak et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,795,430 A | 1/1989 | Quinn et al. |
| 4,803,985 A | 2/1989 | Hill |
| 4,841,888 A | 6/1989 | Mills et al. |
| 4,892,244 A | 1/1990 | Fox et al. |
| 4,899,747 A | 2/1990 | Garren et al. |
| 4,905,693 A | 3/1990 | Ravo |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,146,933 A | 9/1992 | Boyd |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,248,302 A | 9/1993 | Patrick et al. |
| 5,250,058 A | 10/1993 | Miller et al. |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,284,128 A | 2/1994 | Hart |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,358,496 A | 10/1994 | Ortiz et al. |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,508 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,462,559 A | 10/1995 | Ahmed |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,681,263 A | 10/1997 | Flesch |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |
| 5,839,639 A | 11/1998 | Sauer et al. |
| 5,860,581 A | 1/1999 | Robertson et al. |
| 5,861,036 A | 1/1999 | Godin |
| 5,868,141 A | 2/1999 | Ellias |
| 5,868,760 A | 2/1999 | McGuckin, Jr. |
| 5,876,448 A | 3/1999 | Thompson et al. |
| 5,879,371 A | 3/1999 | Gardiner et al. |
| 5,887,594 A | 3/1999 | LoCicero, III |
| 5,888,196 A | 3/1999 | Bonutti |
| 5,897,534 A | 4/1999 | Heim et al. |
| 5,897,562 A | 4/1999 | Bolanos et al. |
| 5,904,147 A | 5/1999 | Conlan et al. |
| 5,906,625 A | 5/1999 | Bito et al. |
| 5,910,105 A | 6/1999 | Swain et al. |
| 5,910,149 A | 6/1999 | Kuzmak |
| 5,921,993 A | 7/1999 | Yoon |
| 5,927,284 A | 7/1999 | Borst et al. |
| 5,928,264 A | 7/1999 | Sugarbaker et al. |

| | | | | | | |
|---|---|---|---|---|---|---|
| 5,935,107 A | 8/1999 | Taylor et al. | | 6,689,062 B1 | 2/2004 | Mesallum |
| 5,938,669 A | 8/1999 | Klaiber et al. | | 6,692,485 B1 | 2/2004 | Brock et al. |
| 5,947,983 A | 9/1999 | Solar et al. | | 6,716,222 B2 | 4/2004 | McAlister et al. |
| 5,964,772 A | 10/1999 | Bolduc et al. | | 6,733,512 B2 | 5/2004 | McGhan |
| 5,964,782 A | 10/1999 | Lafontaine et al. | | 6,736,822 B2 | 5/2004 | McClellan et al. |
| 5,972,001 A | 10/1999 | Yoon | | 6,740,098 B2 | 5/2004 | Abrams et al. |
| 5,972,002 A | 10/1999 | Bark et al. | | 6,740,121 B2 | 5/2004 | Geitz |
| 5,976,161 A | 11/1999 | Kirsch et al. | | 6,746,460 B2 | 6/2004 | Gannoe et al. |
| 5,980,537 A | 11/1999 | Ouchi | | 6,746,489 B2 | 6/2004 | Dua et al. |
| 5,993,464 A | 11/1999 | Knodel | | 6,754,536 B2 | 6/2004 | Swoyer et al. |
| 5,993,473 A | 11/1999 | Chan et al. | | 6,755,849 B1 | 6/2004 | Gowda et al. |
| 6,015,378 A | 1/2000 | Borst et al. | | 6,755,869 B2 | 6/2004 | Geitz |
| 6,030,364 A | 2/2000 | Durgin et al. | | 6,756,364 B2 | 6/2004 | Barbier et al. |
| 6,030,392 A | 2/2000 | Dakov | | 6,764,518 B2 | 7/2004 | Godin |
| 6,042,538 A | 3/2000 | Puskas | | 6,773,440 B2 | 8/2004 | Gannoe et al. |
| 6,044,847 A | 4/2000 | Carter et al. | | 6,773,441 B1 | 8/2004 | Laufer et al. |
| 6,067,991 A | 5/2000 | Forsell | | 6,786,898 B2 | 9/2004 | Guenst |
| 6,074,343 A | 6/2000 | Nathanson et al. | | 6,790,214 B2 | 9/2004 | Kraemer et al. |
| 6,083,241 A | 7/2000 | Longo et al. | | 6,802,868 B2 | 10/2004 | Silverman et al. |
| 6,086,600 A | 7/2000 | Kortenbach | | 6,821,285 B2 | 11/2004 | Laufer et al. |
| 6,113,609 A | 9/2000 | Adams | | 6,830,546 B2 | 12/2004 | Chin et al. |
| 6,119,913 A | 9/2000 | Adams et al. | | 6,835,199 B2 | 12/2004 | McGuckin, Jr. et al. |
| 6,120,513 A | 9/2000 | Bailey et al. | | 6,835,200 B2 | 12/2004 | Laufer et al. |
| 6,136,006 A | 10/2000 | Johnson et al. | | 6,837,848 B2 | 1/2005 | Bonner et al. |
| 6,159,146 A | 12/2000 | El Gazayerli | | 6,840,423 B2 | 1/2005 | Adams et al. |
| 6,159,195 A | 12/2000 | Ha et al. | | 6,845,776 B2 | 1/2005 | Stack et al. |
| 6,165,183 A | 12/2000 | Kuehn et al. | | 6,896,682 B1 | 5/2005 | McClellan et al. |
| 6,179,195 B1 | 1/2001 | Adams et al. | | 6,916,332 B2 | 7/2005 | Adams |
| 6,186,942 B1 | 2/2001 | Sullivan et al. | | 6,926,722 B2 | 8/2005 | Geitz |
| 6,186,985 B1 | 2/2001 | Snow | | 6,966,919 B2 | 11/2005 | Sixto, Jr. et al. |
| 6,197,022 B1 | 3/2001 | Baker | | 6,981,978 B2 | 1/2006 | Gannoe |
| 6,200,318 B1 | 3/2001 | Har-Shai et al. | | 6,991,643 B2 | 1/2006 | Saadat |
| 6,206,822 B1 | 3/2001 | Foley et al. | | 6,994,715 B2 | 2/2006 | Gannoe et al. |
| 6,206,893 B1 | 3/2001 | Klein et al. | | 7,020,531 B2 | 3/2006 | Colliou et al. |
| 6,224,614 B1 | 5/2001 | Yoon | | 7,025,791 B2 | 4/2006 | Levine et al. |
| 6,231,561 B1 | 5/2001 | Frazier et al. | | 7,033,373 B2 | 4/2006 | de la Torre et al. |
| 6,248,058 B1 | 6/2001 | Silverman et al. | | 7,033,378 B2 | 4/2006 | Smith et al. |
| 6,254,642 B1 | 7/2001 | Taylor | | 7,033,384 B2 | 4/2006 | Gannoe et al. |
| 6,273,897 B1 | 8/2001 | Dalessandro et al. | | 7,037,343 B2 | 5/2006 | Imran |
| 6,279,809 B1 | 8/2001 | Nicolo | | 7,037,344 B2 | 5/2006 | Kagan et al. |
| 6,290,674 B1 | 9/2001 | Roue et al. | | 7,059,510 B2 | 6/2006 | Orban, III |
| 6,293,923 B1 | 9/2001 | Yachia et al. | | 7,063,715 B2 | 6/2006 | Onuki et al. |
| 6,302,917 B1 | 10/2001 | Dua et al. | | 7,083,629 B2 | 8/2006 | Weller et al. |
| 6,312,437 B1 | 11/2001 | Kortenbach | | 7,083,630 B2 | 8/2006 | DeVries et al. |
| 6,328,689 B1 | 12/2001 | Gonzalez et al. | | 7,087,011 B2 | 8/2006 | Cabiri et al. |
| 6,334,865 B1 | 1/2002 | Redmond et al. | | 7,097,650 B2 | 8/2006 | Weller et al. |
| 6,338,345 B1 | 1/2002 | Johnson et al. | | 7,160,312 B2 | 1/2007 | Saadat |
| 6,352,543 B1 | 3/2002 | Cole | | 7,520,884 B2 | 4/2009 | Swanstrom et al. |
| 6,358,197 B1 | 3/2002 | Silverman et al. | | 7,666,195 B2 | 2/2010 | Kelleher et al. |
| 6,379,366 B1 | 4/2002 | Fleischman et al. | | 2001/0014800 A1 | 8/2001 | Frazier et al. |
| 6,387,104 B1 | 5/2002 | Pugsley, Jr. et al. | | 2001/0020190 A1 | 9/2001 | Taylor |
| 6,398,795 B1 | 6/2002 | McAlister et al. | | 2001/0037127 A1 | 11/2001 | De Hoyos Garza |
| 6,416,535 B1 | 7/2002 | Lazarus | | 2002/0022851 A1 | 2/2002 | Kalloo et al. |
| 6,423,087 B1 | 7/2002 | Sawada | | 2002/0035361 A1 | 3/2002 | Houser et al. |
| 6,432,040 B1 | 8/2002 | Meah | | 2002/0040226 A1 | 4/2002 | Laufer et al. |
| 6,447,533 B1 | 9/2002 | Adams | | 2002/0047036 A1 | 4/2002 | Sullivan et al. |
| 6,460,543 B1 | 10/2002 | Forsell | | 2002/0058967 A1 | 5/2002 | Jervis |
| 6,475,136 B1 | 11/2002 | Forsell | | 2002/0072761 A1 | 6/2002 | Abrams et al. |
| 6,491,707 B2 | 12/2002 | Makower et al. | | 2002/0077661 A1 | 6/2002 | Saadat |
| 6,494,888 B1 | 12/2002 | Laufer et al. | | 2002/0078967 A1 | 6/2002 | Sixto, Jr. et al. |
| 6,506,196 B1 | 1/2003 | Laufer | | 2002/0082621 A1 | 6/2002 | Schurr et al. |
| 6,535,764 B2 | 3/2003 | Imran et al. | | 2002/0143346 A1 | 10/2002 | McGuckin, Jr. et al. |
| 6,540,789 B1 | 4/2003 | Silverman et al. | | 2002/0165589 A1 | 11/2002 | Imran et al. |
| 6,551,310 B1 | 4/2003 | Ganz et al. | | 2002/0183765 A1 | 12/2002 | Adams |
| 6,554,844 B2 | 4/2003 | Lee et al. | | 2002/0183768 A1 * | 12/2002 | Deem et al. .................. 606/151 |
| 6,558,400 B2 | 5/2003 | Deem et al. | | 2002/0193816 A1 | 12/2002 | Laufer et al. |
| 6,561,969 B2 | 5/2003 | Frazier et al. | | 2003/0040804 A1 | 2/2003 | Stack et al. |
| 6,572,629 B2 | 6/2003 | Kalloo et al. | | 2003/0040808 A1 | 2/2003 | Stack et al. |
| 6,579,301 B1 | 6/2003 | Bales et al. | | 2003/0065340 A1 | 4/2003 | Geitz |
| 6,592,596 B1 | 7/2003 | Geitz | | 2003/0065359 A1 | 4/2003 | Weller et al. |
| 6,605,037 B1 | 8/2003 | Moll et al. | | 2003/0093117 A1 * | 5/2003 | Saadat .......................... 606/221 |
| 6,626,899 B2 | 9/2003 | Houser et al. | | 2003/0109892 A1 | 6/2003 | Deem et al. |
| 6,632,227 B2 | 10/2003 | Adams | | 2003/0109931 A1 | 6/2003 | Geitz |
| 6,656,194 B1 | 12/2003 | Gannoe et al. | | 2003/0109935 A1 | 6/2003 | Geitz |
| 6,663,598 B1 | 12/2003 | Carrillo, Jr. et al. | | 2003/0120265 A1 | 6/2003 | Deem et al. |
| 6,663,639 B1 | 12/2003 | Laufer et al. | | 2003/0120285 A1 | 6/2003 | Kortenbach |
| 6,663,640 B2 | 12/2003 | Kortenbach | | 2003/0120289 A1 | 6/2003 | McGuckin, Jr. et al. |
| 6,675,809 B2 | 1/2004 | Stack et al. | | 2003/0132267 A1 | 7/2003 | Adams et al. |
| 6,682,520 B2 | 1/2004 | Ingenito | | 2003/0158563 A1 | 8/2003 | McClellan et al. |

| | | |
|---|---|---|
| 2003/0158601 A1 | 8/2003 | Silverman et al. |
| 2003/0171760 A1 | 9/2003 | Gambale |
| 2003/0183765 A1 | 10/2003 | Chen et al. |
| 2003/0208209 A1 | 11/2003 | Gambale et al. |
| 2003/0216754 A1 | 11/2003 | Kraemer et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0024386 A1 | 2/2004 | Deem et al. |
| 2004/0030347 A1 | 2/2004 | Gannoe et al. |
| 2004/0034371 A1 | 2/2004 | Lehman et al. |
| 2004/0037865 A1 | 2/2004 | Miller |
| 2004/0039452 A1 | 2/2004 | Bessler |
| 2004/0044354 A1 | 3/2004 | Gannoe et al. |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0088008 A1 | 5/2004 | Gannoe et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1* | 7/2004 | Cartledge et al. ............ 623/2.37 |
| 2004/0148034 A1 | 7/2004 | Kagan et al. |
| 2004/0158331 A1 | 8/2004 | Stack et al. |
| 2004/0162568 A1 | 8/2004 | Saadat |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0210243 A1 | 10/2004 | Gannoe et al. |
| 2004/0215180 A1 | 10/2004 | Starkebaum et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2004/0236357 A1 | 11/2004 | Kraemer et al. |
| 2004/0249362 A1 | 12/2004 | Levine et al. |
| 2005/0010162 A1 | 1/2005 | Utley et al. |
| 2005/0021681 A1 | 1/2005 | Oommen |
| 2005/0027307 A1 | 2/2005 | Schwartz et al. |
| 2005/0033328 A1 | 2/2005 | Laufer et al. |
| 2005/0038415 A1 | 2/2005 | Rohr et al. |
| 2005/0038462 A1 | 2/2005 | Lubock et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080438 A1 | 4/2005 | Weller et al. |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0119671 A1 | 6/2005 | Reydel et al. |
| 2005/0119674 A1 | 6/2005 | Gingras |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0192599 A1 | 9/2005 | Demarais |
| 2005/0192601 A1 | 9/2005 | Demarais |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0203547 A1 | 9/2005 | Weller et al. |
| 2005/0203548 A1 | 9/2005 | Weller et al. |
| 2005/0228415 A1 | 10/2005 | Gertner |
| 2005/0228504 A1 | 10/2005 | Demarais |
| 2005/0247320 A1* | 11/2005 | Stack et al. .................. 128/898 |
| 2005/0256533 A1 | 11/2005 | Roth et al. |
| 2005/0256587 A1 | 11/2005 | Egan |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |
| 2006/0106288 A1 | 5/2006 | Roth et al. |
| 2006/0111735 A1 | 5/2006 | Crainich |
| 2006/0122462 A1 | 6/2006 | Roth et al. |
| 2006/0142787 A1 | 6/2006 | Weller et al. |
| 2006/0151568 A1 | 7/2006 | Weller et al. |
| 2007/0208360 A1 | 9/2007 | Demarais et al. |
| 2007/0213740 A1 | 9/2007 | Deem et al. |
| 2007/0213748 A1 | 9/2007 | Deem et al. |
| 2007/0219570 A1 | 9/2007 | Deem et al. |
| 2007/0233161 A1 | 10/2007 | Weller et al. |
| 2007/0233162 A1 | 10/2007 | Gannoe et al. |
| 2007/0250083 A1 | 10/2007 | Deem et al. |
| 2007/0282349 A1 | 12/2007 | Deem et al. |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| FR | 2 768 324 A1 | 3/1999 |
| JP | 63277063 A | 11/1988 |
| JP | 63279854 | 11/1988 |
| JP | 63302863 A | 12/1988 |
| JP | 01049572 A | 2/1989 |
| JP | 04297219 | 10/1992 |
| WO | WO 94/18893 A1 | 9/1994 |
| WO | WO 99/17662 A1 | 4/1999 |
| WO | WO 99/53827 A1 | 10/1999 |
| WO | WO 00/07640 A2 | 2/2000 |
| WO | WO 00/32137 A1 | 6/2000 |
| WO | WO-0039708 A1 | 7/2000 |
| WO | WO 00/48656 A1 | 8/2000 |
| WO | WO 00/78227 A1 | 12/2000 |
| WO | WO 00/78229 A1 | 12/2000 |
| WO | WO 01/26557 A1 | 4/2001 |
| WO | WO 01/28432 A1 | 4/2001 |
| WO | WO 01/66018 A1 | 9/2001 |
| WO | WO 01/67964 A2 | 9/2001 |
| WO | WO 01/85034 A1 | 11/2001 |
| WO | WO 02/24080 A2 | 3/2002 |
| WO | WO 02/35980 A2 | 5/2002 |
| WO | WO 02/39880 A2 | 5/2002 |
| WO | WO-0239880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |
| WO | WO 03/099140 A1 | 12/2003 |
| WO | WO 03/105563 A2 | 12/2003 |
| WO | WO 03/105671 A2 | 12/2003 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO-2004/019788 A2 | 3/2004 |

| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | WO 2006/078781 A1 | 7/2006 |

OTHER PUBLICATIONS

Benjamin, S.B., *Small Bowel Obstruction and the Garren-Edwards Bubble, Lessons to be Learned?* Abstracts Submitted to A/S/G/E 1987, Division of Gastroenterology, Department of Medicine, Georgetown University Hospital, Washington, D.C.

Boyle, Thomas M., M.D., et al., Small Intestinal Obstruction Secondary to Obturation by a Garren Gastric Bubble, *The American Journal of Gastroenterology*, vol. 82, No. 1, pp. 51-53, 1987.

Büchler, M.W., M.D. et al., A Technique for Gastroplasty As A Substitute For The Esophagus: Fundus Rotation Gastroplasty, *Journal of The American College of Surgeons*, vol. 182, pp. 241-245, Mar. 1996.

Cass, O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D.[1], et al.. Gastro-Clip® Gastroplasty: A Very Long-Term Complication, *Obesity Surgery*, 14, © FD-Communications Inc.. 2004.

Clark, Charlene, R.N., The Gastric Bubble: Medicine, Magic or Mania? *SGA Journal*, vol. 9, No. 2, pp. 45-47, Fall 1986.

Cummings, David E., M.D., et al., Plasma Ghrelin Levels After Diet-Induced Weight Loss or Gastric Bypass Surgery, *New England Journal of Medicine*, vol. 346, No. 21, pp. 1623-1630, May 23, 2002.

Davenport, Horace W., Ph.D., D.Sc., *Physiology of the Digestive Tract: An Introductory Text*, 3d Ed., Cover and Table of Contents.

DeMeester, Tom T., M.D., Evolving Concepts of Reflux: The Ups and Downs of the LES, *Canadian Journal of Gastroenterology*, vol. 16, No. 5, pp. 327-331, 2002.

De Waele, B., M.D., et al., Intragastric Balloons for Preoperative Weight Reduction, *Obesity Surgery*, vol. 10, pp. 58-60, 2000.

Edell, Steven L., et al., Radiographic Evaluation of the Garren Gastric Bubble, *American Journal of Radiology*, vol. 145, pp. 49-50, Jul. 1985.

Endo Gia* Universal, Single UseStapler and Endo GIA Roticulator*, Brochure, 8 pages, Undated.

Filipi, Charles J. M.D., et al., Transoral, Flexible Endoscopic Suturing For Treatment Of GERD: A Multicenter Trial, *Gastrointestinal Endoscopy*, vol. 53, No. 4, pp. 416-422, 2001.416-422, 2001.

Gray, Henry, R.R.S., *Anatomy of the Human Body*, The Digestive System, Thirtieth American Edition, pp. 1466-1467 (Undated).

Guidant, Internet, AXIUS™ VACUUM 2 Stabilizer Systems, Internet Website— www.guidant.com/products/axius_vacuum.shtml, 8 pages, visited May 27, 2003.

Gukovsky-Reicher, S., M.D. et al., *Expandable Metal Esophageal Stents: Efficacy and Safety. Review of Current Literature Data and of 53 Stents Placed at Harbor-UCLA Medical Center*, www.medscape.com/viewarticle/423508_print_pp. 1-20, Medscape General Medicine 4(1), 2003 © 2002 Medscape, downloaded Oct. 9, 2006.

Hepworth, Clive C. FRCS et al., Mechanical Endoscopic Methods Of Haemostasis For Bleeding Peptic Ulcers: A Review, *Bailliere's Clinical Gastroenterology*, vol. 14, No. 3 pp. 467-476, 2000.

Ikeda, Y. et al., New Suturing Device For Transanal Endoscopic Microsurgery, *Blackwell Science Ltd*. p. 1290, 1997.

Johnson & Johnson Gateway[sm] Endopath 3mm, 5mm and 10 mm Diameter Endoscopic Instruments, Internet Website—www.inigateway.com/home.ihtml?loc=USENG&page=viewContent&parentId-0900..., 3 pages, visited May 29, 2003.

Kirby, Donald F., Incomplete Small Bowel Obstruction by the Garren-Edwards Gastric Bubble Necessitating Surgical Intervention, *The American Journal of Gastroenterology*, vol. 82, No. 3, pp. 251-253, 1987.

Nieben, Ole Gyring, et al., Intragastric Balloon as an Artificial Bezoar for Treatment of Obesity, *The Lancet*, pp. 198-199, Jan. 23, 1982.

Percival, Walter L., M.D., "The Balloon Diet": A Noninvasive Treatment for Morbid Obesity. Preliminary Report of 1908 Patients, *The Canadian Journal of Surgery*, vol. 27, No. 2, pp. 135-136.

Power Medical Interventions Digital and Wireless Medical Technology, Product Innovation: SurgASSIST™, Internet Website—www/pmi2.com/access_flexibility.asp, 6 pages, visited May 29, 2003.

Snowden Pencer, Diamon-Flex Angled Snake Retractor (class 1, 878.4800), Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., An Endoscopic Sewing Machine, *Gastrointestinal Edoscopy*, vol. 32, No. 1 pp. 36-38, 1986.

Swain, C. Paul, M.D., Endoscopic Sewing And Stapling Machines, *Endoscopy* pp. 205-210, © Georg Thieme Verlag Stuttgart, New York, 1997.

Swain, C. Paul, M.D. et al., An Endoscopic Stapling Device: The Development of A New Flexible Endoscopically Controlled Device For Placing Multiple Transmural Staples In Gastrointestinal Tissue, *Gastrointestinal Endoscopy*, vol. 35, No. 4, pp. 338-339, 1989.

Swain, C. Paul, M.D., Endoscopic Suturing, *Bailliere's Clinical Gastroenterology*, Bailliere's Tindall,, vol. 13 No. 1, pp. 97-108, 1999.

Taylor, T. Vincent, et al., Gastric Balloons for Obesity, *The Lancet*, Abstract, Mar. 27, 1982.

Vandenplas, Y., et al., Intragastric Balloons in Adolescents With Morbid Obesity, *European Journal of Gastroenterology & Hepatology*, vol. 11, No. 3, pp. 243-245, 1999.

Villar, Hugo V., M.D., et al., Mechanisms of Satiety and Gastric Emptying After Gastric Partitioning and Bypass, *Surgery*, pp. 229-236, Aug. 1981.

Wullstein, C., et al., Compression Anastomosis (AKA-2) in Colorectal Surgery: Results in 442 Consecutive Patients, *British Journal of Surgery 2000*, pp. 1071-1075.

U.S. Appl. No. 10/773,883, filed Feb. 5, 2004 unpublished; Inventors: Gerbi et al. cited by other.

U.S. Appl. No. 10/797,439, filed Mar. 9, 2004 unpublished; Inventors: Weller et al. cited by other.

Buchler, M.W., M.D. et al., A Technique For Gastroplasty As A Substitute For the Esophagus: Fundus Rotation Gastroplasty, Journal Of The American College of Surgeons, vol. 182, pp. 241-245, Mar. 1996. cited by other.

* cited by examiner

METHODS AND DEVICES FOR REDUCING HOLLOW ORGAN VOLUME

CROSS-REFERENCE TO RELATED APPLICATION

This application is a division of U.S. Ser. No. 11/067,598 filed Feb. 25, 2005, which claims priority to U.S. Provisional Application Ser. No. 60/547,961 filed Feb. 27, 2004, the contents of both of which are incorporated herein by reference.

BACKGROUND OF THE INVENTION

1. Field of the Invention

The present invention pertains to medical equipment and more particularly to mechanical methods for reducing the volume of the stomach for the treatment of obesity.

2. General Background and State of the Art

Approximately 64% of Americans are overweight and obesity is rapidly becoming an epidemic resulting in a multitude of co-morbidities (e.g. cardiovascular disease, diabetes, etc.) and enormous medical costs. Approximately $75 billion dollars are spent each year on weight-related diseases in the US alone.

Historically, methods of weight reduction have ranged from oral pharmacological means, a multitude of diets, and various exercise programs. These approaches have generally resulted in temporary weight loss, with no or limited long-term benefit.

In recent years, the concept of obesity being a disease has gained momentum. To that end, surgical treatments have been developed to provide a more permanent solution (e.g. stomach stapling, gastric bypass, and the like). However, these treatments are generally surgical in nature, which imply inherent risk and high cost to the patient.

Thus, it remains desirable to develop new alternatives to provide non-invasive or minimally-invasive solutions to obesity.

SUMMARY OF THE INVENTION

The present invention overcomes some or all of the shortcomings of the current techniques by providing a minimally-invasive placement of a mechanical structure for reducing the volume of the stomach via an esophageal approach.

One embodiment involves esophageal delivery of a mechanical structure into the stomach wall. The structure consists of an adjustable band, which is delivered in a collapsed configuration via endoscopic guidance. Once in position, the band is mechanically or self expanded until it contacts the stomach wall. The band is then attached to the wall via hooks, anchors, staples, sutures, or other means. Once attached, the device is mechanically collapsed to the desired stricture size, resulting in a reduction in stomach volume. In one embodiment, a standard endoscope is compatible with the delivery system, but an endoscope may also be integrated into the delivery system. The adjustable band may be constructed from stainless steel, shape-memory alloys, various polymers, or a composite and is attached to the stomach wall via sutures, various crimping techniques (e.g. staples), rivets, or the like. The above procedure may be performed more than once to create multiple strictures and achieve the desired volume reduction.

In another embodiment, an intragastric band is formed of a shape-memory alloy, such as nitinol. The shape-memory band can be expanded by applying force to the band and then secured to the stomach wall via sutures, anchors, or the like. After the shape-memory band is secured to the stomach wall, the force expanding the shape-memory band is removed, and the shape-memory band returns to a relaxed configuration having a smaller diameter than in the expanded configuration. As the shape-memory band returns to its relaxed configuration, it forms a stricture within the stomach cavity, thereby reducing the volume of the stomach cavity.

A calibration mechanism may also be designed into the system to control the size of the stricture to be created. The mechanism may take the form of a non-compliant or semi-compliant balloon, which may be inflated to a desired diameter. Said mechanism may also be comprised of a mechanically-expanding device. The band may then be collapsed until it contacts the calibration device.

It may also be desirable to adjust the size of the stricture post-procedure. One method for adjusting the stricture size could be to use an adjusting device, which is endoscopically guided. The adjusting device is matingly engaged to the band and is rotated to loosen or tighten the band.

An alternative embodiment involves esophageal delivery of a tensioning member, which is a suture or the like stitched to a polymer fabric or mesh ribbon or band (i.e., in a purse-string suture manner) which is further attached to the stomach wall via adhesive or other previously-described anchoring means, incorporated herein by reference. Multiple stitches are placed in the fabric/mesh to define a circumference and a cinching device is utilized to apply tension the tensioning member, resulting in a volume reduction. The cinching device is then used to secure the tensioning member (e.g. a knot, clip, etc.) and disconnect it. This procedure may also be performed more than once to create multiple strictures in the stomach.

It may also be desirable to adjust the size of the stricture post-procedure. The preferred method for adjusting the stricture size could be to allow for the termination of the tensioning member (e.g. suture) to be mechanical in nature (rather than a knot) and allow for additional suture to be available for loosening the stricture. The suture could be on a spool or other system such that the suture could also be tightened. Alternatively, the original tensioning member could be severed and removed, and an accessory device may be provided to restring the anchors back together to achieve an alternative constriction in the stomach.

Multiple devices may be used to optimally place these bands and tensioning member, apply tension to cinch the stomach wall together, secure the tensioning member, terminate the tensioning member, and visualize the procedure.

An alternative method for reducing stomach volume may be to attach or bond folds of tissue together. An adhesive delivery system is used to gather folds of tissue and subsequently dispense adhesive into the folds resulting in a permanent or temporary bond. Alternatively, clips or other mechanical means may be used instead of adhesive or in conjunction with adhesive. By creating one single large fold, or a plurality of folds, the volume of the stomach may be reduced.

The delivery system may incorporate a balloon which is inflated in the esophagus to facilitate applying positive or negative pressure to the entire stomach to facilitate placing devices described herein.

DETAILED DESCRIPTION OF THE PREFERRED EMBODIMENTS

As will be discussed in detail below, a method of reducing the volume of the stomach involves creating strictures or stomas within the stomach cavity. These strictures can be created through minimally-invasive placement of a mechanical structure for reducing the volume of the stomach via an esophageal approach. For ease of reference, the following embodiments will be described as being advanced transorally to the stomach, although the embodiments of the restricting devices can be used in conjunction with surgical techniques, such as laparoscopic tools to assist in visualization, placement or anchoring, and may be used within other hollow body organs as well.

Figure 1:
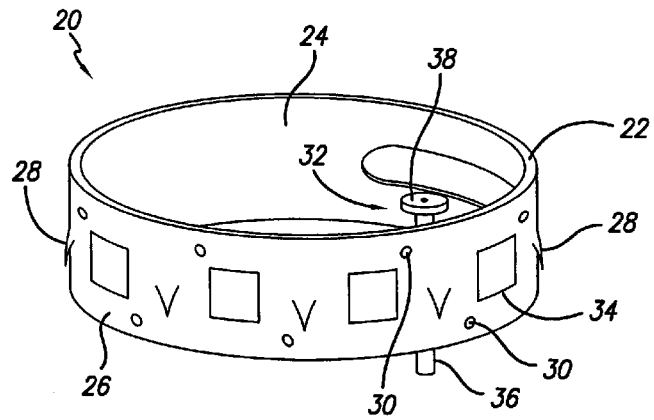
FIG. 1 depicts a perspective view of an intragastric band.

In one embodiment, an intragastric band 20 is secured to the stomach wall and then tightened to form a stricture within the stomach. As shown in FIG. 1, the mechanical intragastric band includes a generally circular body 22 having an inner surface 24 and an outer surface 26. The outer surface may include hooks or barbs 28 for initial fixation to the stomach lining. Also, the circular body may include fenestrations 30 located along the entire circular body. Additional anchors or staples may be placed through the fenestrations for attaching the intragastric band to the stomach. In another embodiment, sutures may be used to attach the band to the stomach wall through the fenestrations. Further, the intragastric band includes an adjustment mechanism 32 that adjusts the diameter of the intragastric band. Located around the circular body are notches or size-adjustment steps 34 that cooperate with the adjustment mechanism to vary the size of the band. The intragastric band is very similar to a common hose clamp, and is adjusted in the same manner. The adjustment mechanism includes a screw 36 with a screw head 38, which can be tightened to secure the size of the band, or loosened to adjust the size of the band.

In use, the intragastric band 20 is delivered to the stomach cavity in a collapsed configuration, and then expanded until it contacts the inner wall of the stomach. As the band expands, the hooks or barbs 28 help secure the band to the stomach wall. The band may be self expanding or can be expanded mechanically using the adjustment mechanism. Anchors, rivets, sutures, or other means are then used to secure the intragastric band to the stomach wall through the fenestrations 30 provided through the circular body 22 of the band. The band may also be secured to the stomach wall using an adhesive. Once secure, the diameter of the band is decreased by moving the adjustment mechanism 32 into the appropriate notch or adjustment step 34 until the desired size is achieved, drawing the stomach wall with the band as it decreases, thereby creating a stricture within the stomach cavity. The size of the band is then secured by tightening the adjustment mechanism with the screw head 36. The intragastric band cinches the stomach wall, thereby reducing the stomach volume.

At any time after the procedure, the size of the stricture formed with the intragastric band 20 may adjusted by moving the adjustment mechanism 32 with an adjustment tool under endoscopic guidance. The adjustment tool would be similar to a flexible screw driver and would allow for increasing or decreasing the size of the band by turning the screw 36 of the adjustable mechanism 32. In one embodiment, the adjustment tool may be incorporated into the band delivery system or provided as a separated component. In use, the adjustment tool may mechanically engage the screw head 38, much like a screw driver, or a magnetic force could be used to move the adjustable mechanism. Both the screw of the adjustable mechanism and the adjustment tool may be magnetized such that they are drawn together, engage, and be utilized to adjust the size of the band.

Figure 2:
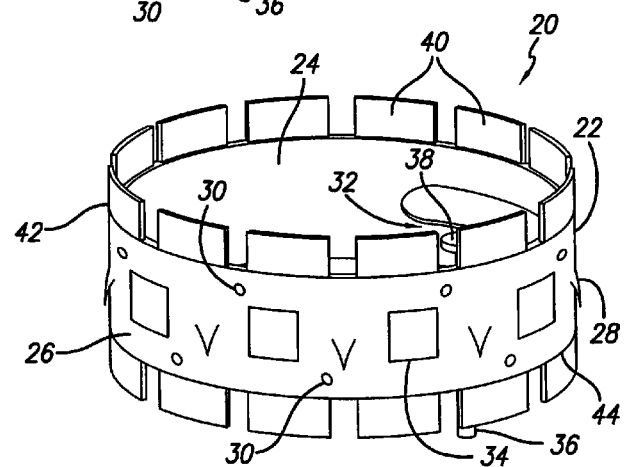
FIG. 2 depicts a perspective view of another embodiment of the intragastric band of FIG. 1.
Figure 3:
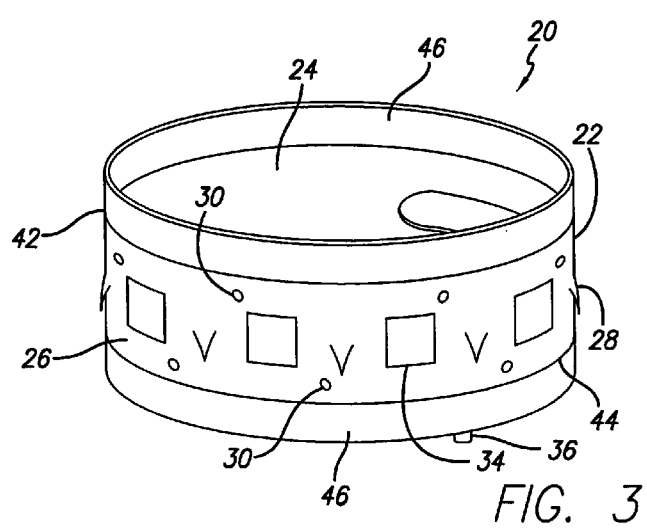
FIG. 3 depicts a perspective view of yet another embodiment of the intragastric band of FIG. 1.

Another embodiment of the intragastric band 20 is shown in FIG. 2, with like reference numerals referencing like or similar details. In this embodiment of the mechanical band, fabric tabs 40 are disposed around the circumference and on a first end 42 and a second end 44 of the circular body 22. In another embodiment, a continuous strip of fabric 46 can be disposed on both the first and second ends of the circular body as shown in FIG. 3. The fabric component may be polyester, PTFE, ePTFE, PET, non-woven, woven, a braided material or mesh, or combination braid or mesh incorporating a fabric and a metal component (produced by Secant Medical, Perkasie, Pa.), etc. Any type of the anchor, staple, or suture may be attach to the stomach wall through the fabric tabs, thereby securing the intragastric band to the stomach wall. In addition, the band may also be secured to the stomach with additional anchors positioned through the fenestrations 30. Further, an adhesive may be used to bond the fabric to the stomach wall.

Figure 4A:
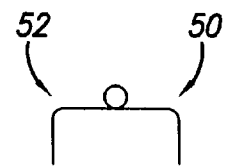
FIGS. 4a through 6 depict types of anchors.
Figure 4B:
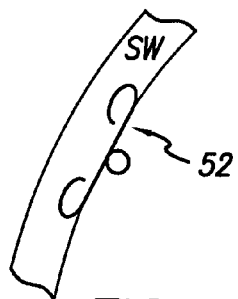
Figure 5A:
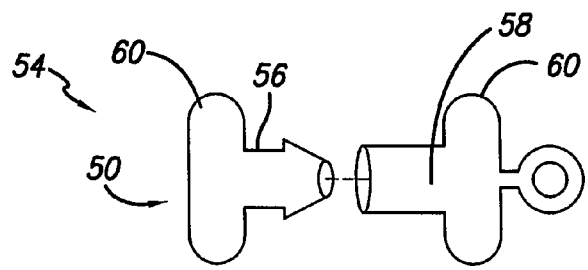
Figure 5B:
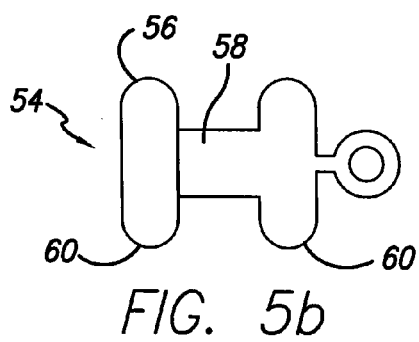
Figure 6:
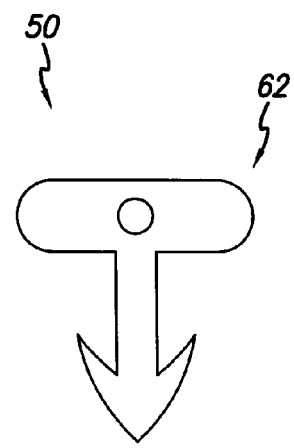

As discussed above, anchors 50 may be used to secure the intragastric band to the stomach wall. FIGS. 4a through 6 show different embodiments of anchors that may be inserted through the fenestrations 30, fabric tabs, or fabric strip of the mechanical intragastric band. FIG. 4a depicts a staple 52, and FIG. 4b depicts the staple crimped into the stomach wall. A rivet 54 is shown in FIG. 5a having a male portion 56 and a female portion 58. The band could be secured between flanges 60 of the rivet when the male portion is mated with the female portion as shown in FIG. 5b. Another embodiment of an anchor 62 is shown in FIG. 6. These anchors and others are disclosed in U.S. Ser. No. 11/056,327, the entire contents of which are incorporated herein by reference. Any other type of anchor may also be used to secure the intragastric band to the stomach.

Figure 7:
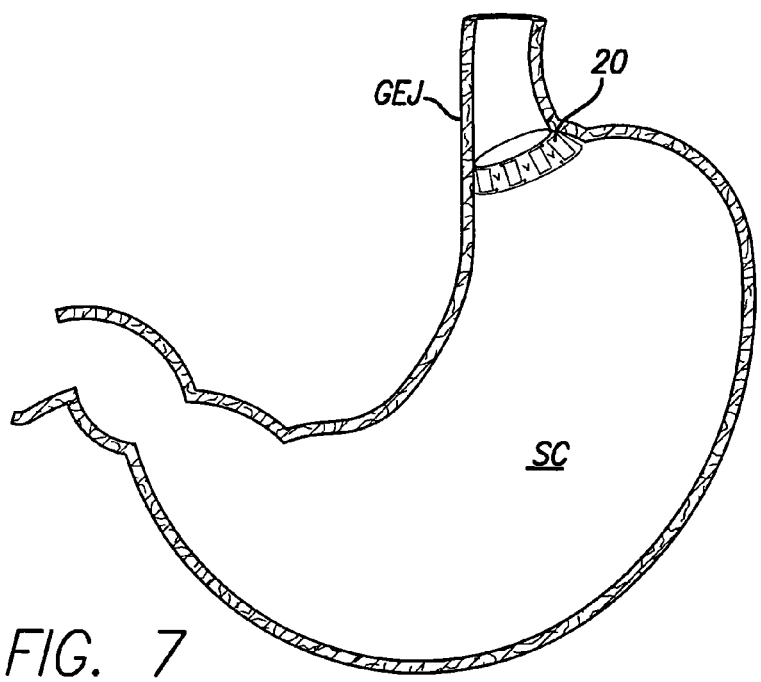
FIG. 7 depicts a schematic view of the intragastric band of FIG. 1 placed within the stomach cavity.
Figure 8:
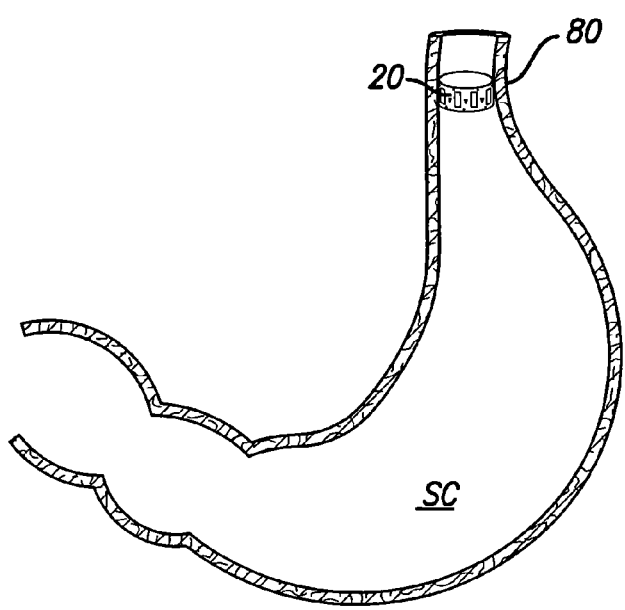
FIG. 8 depicts a schematic view of the intragastric band of FIG. 7 after reducing its diameter to form a stricture within the stomach cavity.

FIG. 7 depicts the intragastric band 20 secured within the stomach cavity SC near the gastro esophageal junction ("GEJ"). The band may however be positioned anywhere along the stomach cavity between the GEJ and the pylorus. After the size of the band is decreased, taking the stomach tissue with it, a stricture 80 is formed, as shown in FIG. 8, thereby reducing the volume of the stomach cavity. Further, multiple bands may be secured within the stomach cavity to form multiple strictures or stomas within the stomach cavity.

Figure 9:
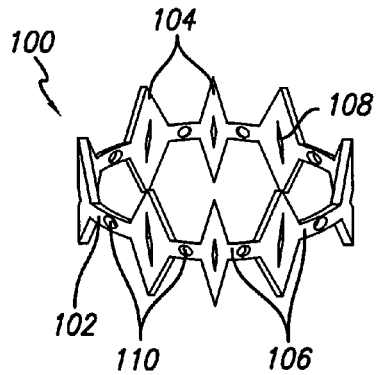
FIG. 9 depicts a perspective view of a shape-memory intragastric band in a relaxed state.
Figure 10:
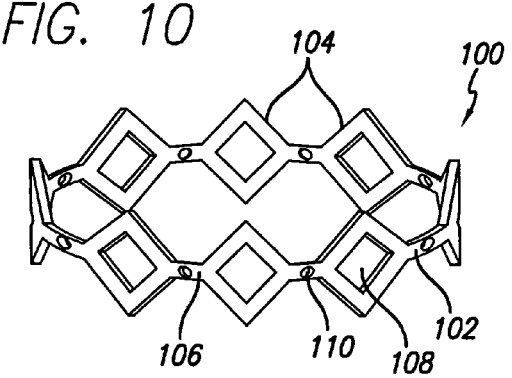
FIG. 10 depicts a perspective view of the shape-memory intragastric band of FIG. 9 in an expanded state.

Another embodiment of an intragastric band 100 is shown in FIGS. 9 and 10. The band is formed of a shape-memory material, such as nitinol, and is self-collapsing. The shape-memory band includes a generally circular body 102 having a plurality of expandable sections 104 and connecting strips 106 disposed in between the expandable sections. In this embodiment, the expandable section is diamond shaped and includes an opening 108 that allows the expandable sections to expand and contract. The expandable sections may also be formed in any shape, including circular or oval. In an alternative embodiment, only the expandable sections of the band may include nitinol. In another embodiment, the expandable sections may be connected directly to one another without the connecting strips disposed in between. This configuration would reduce the diameter of the shape-memory band. Eyelets or fenestrations 110 are disposed in the body of the band, and in one embodiment are positioned within the connecting strips. FIG. 9 depicts the shape-memory band in its relaxed, unexpanded configuration, with the openings of the expandable section nearly closed. The band is delivered to the stomach cavity in this unexpanded configuration. After the band is positioned within the stomach cavity, the band can be mechanically expanded with a delivery device transitioning the shape-memory band into an expanded configuration as shown in FIG. 10. In the expanded configuration, the openings within the expandable sections increases to allow the band to increase its diameter. During the procedure, the expanded band comes into contact with the stomach wall, and anchors or sutures are used to secure the expanded band to the stomach wall through the fenestrations. In one embodiment, a vacuum is applied to the stomach cavity to bring the stomach wall into contact with the intragastric band, and then the band is secured to the stomach wall. Once secured to the stomach wall, the mechanical force applied by the delivery device is removed from the band, allowing the band to return to its relaxed unexpanded configuration, thereby decreasing its diameter. As the band's diameter decreases, the attached portion of the stomach wall is also drawn to a smaller diameter forming a stricture or stoma. It should be noted that the size of the shape-memory band's diameter in its relaxed state is predetermined to form strictures of varying sizes.

Figure 12:
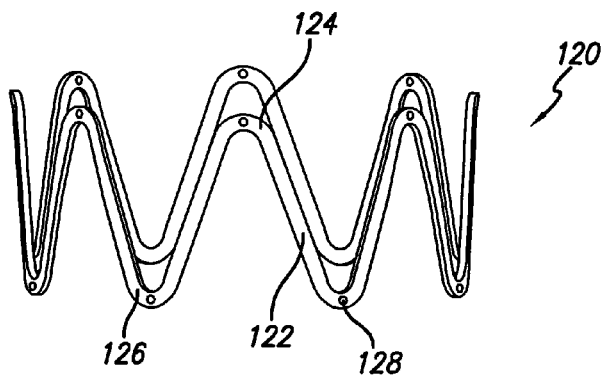
FIG. 12 depicts a perspective view of the shape-memory intragastric band of FIG. 11 in an expanded state.
Figure 11:
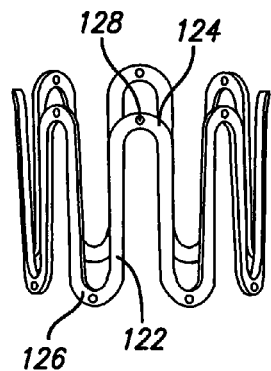
FIG. 11 depicts a perspective view of a another embodiment of a shape-memory intragastric band in a relaxed state.

Yet another embodiment of an intragastric band 120 is shown in FIGS. 11 and 12. In this embodiment, the band includes a generally serpentine or undulating body 122 having peaks 124 and valleys 126. The body of the band is formed of a shape-memory material, such as nitinol. Eyelets or fenestrations 128 are formed within the body of the band, which allow anchors or suture to secure the band to the stomach wall. The fenestrations can be positioned anywhere along the body of the band, however, in one embodiment, the fenestrations are positioned near the peaks and valleys of the band. FIG. 11 depicts the shape-memory band in a relaxed, unexpanded configuration, with relatively little distance between adjacent peaks and valleys. The band is delivered to the stomach cavity in this unexpanded configuration. After the band is positioned within the stomach cavity, the band can be mechanically expanded with a delivery device to transition the shape-memory band into an expanded configuration as shown in FIG. 12. In the expanded configuration, the distance between adjacent peaks and valleys increases, allowing the band to increase its diameter. In use, the expanded band comes into contact with the stomach wall and anchors or sutures are used to secure the expanded band to the stomach wall through the fenestrations. In one embodiment, a vacuum is applied to the stomach cavity to bring the stomach wall into contact with the intragastric band, and then the band is secured to the stomach wall. Once secured to the stomach wall, the mechanical force applied by the delivery device is removed from the band, allowing the shape-memory band to return to its relaxed unexpanded configuration, decreasing its diameter. As the band's diameter decreases, the attached portion of the stomach wall is also drawn to a smaller diameter forming a stricture or stoma.

Figure 13:
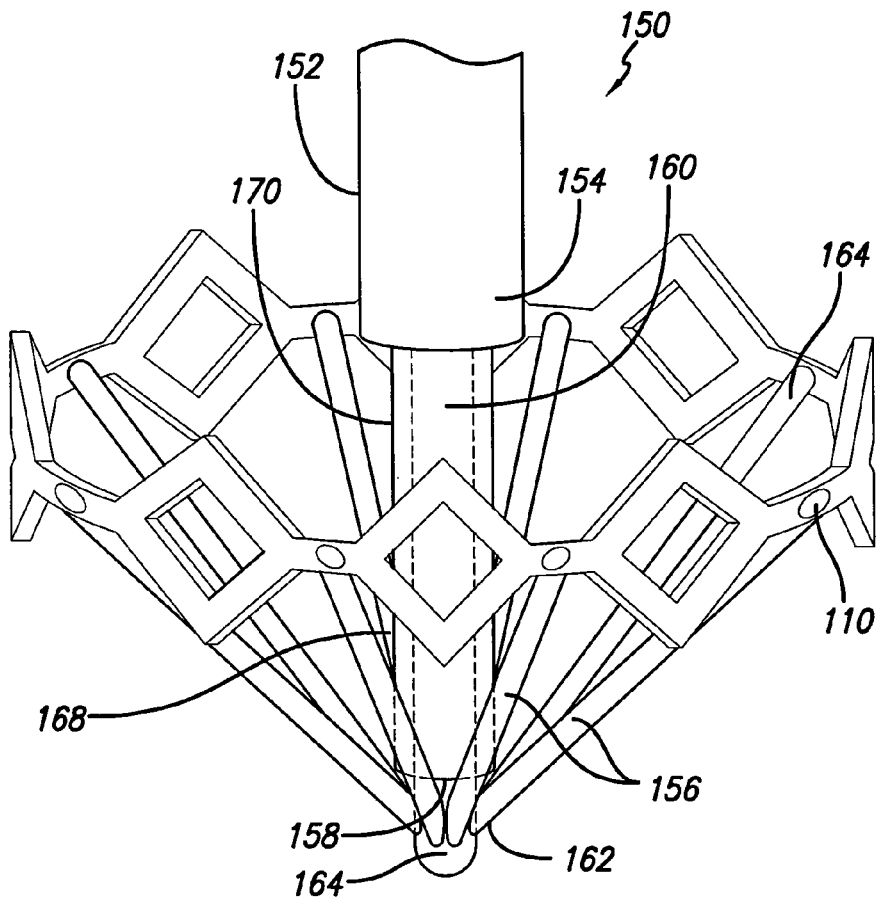
FIG. 13 depicts a partial view of a delivery device for expanding and securing the shape-memory intragastric band.

Referring now to FIG. 13, a delivery device 150 is shown that can position and secure the shape-memory bands 100 and 120 to the stomach wall. The delivery system includes a delivery sheath 152, which has a distal end 154 and a proximal end (not shown). The delivery sheath houses at least two articulating members or delivery tubes 156 that are flexibly or hingedly attached to a distal end 158 of a central rod 160. The delivery tubes each have an attached end 162 and an ejection end 164. At the distal end of the rod is an atraumatic tip such as a nosecone 166. The system also includes a pusher 168 attached to a hollow tube 170 that is disposed over the central rod. Anchors may be positioned near the ejection end of the delivery tubes. The shape-memory band may be housed within the delivery sheath in its relaxed unexpanded configuration or in a more constricted state. In another embodiment, the shape-memory band may be delivered to the stomach cavity in a separate delivery sheath.

During the procedure, the distal end 154 of the delivery system 150 is delivered down the esophagus to the stomach cavity under endoscopic guidance. As the system is delivered, the plurality of delivery tubes 156 are folded inside the delivery sheath 152. Once in position within the stomach cavity, the delivery sheath is pulled proximally while the central rod is held in position to release the delivery tubes. Next, the pusher 168 is pushed distally until it comes into contact with the attached ends 160 of the delivery tubes to expand the delivery tubes into an expanded configuration as shown in FIG. 13. The shape-memory band is positioned on the delivery tubes so that as the delivery tubes expand, they force the shape-memory band into its expanded configuration to come into contact with the stomach wall. A vacuum may also be applied to the stomach cavity at this time to bring the stomach wall into contact with the shape-memory band. As shown in the figure, the ejection ends 164 of the delivery tubes are in-line with the fenestrations 110 of the shape-memory band. To secure the band to the stomach wall, anchors may be ejected from the ejection ends of the delivery tubes, through the fenestrations 110 or 128 of the band and into the stomach wall. In one embodiment, the anchors are ejected by a pneumatic pressure. In this embodiment, the central rod can provide a pathway to direct air pressure to the delivery tubes to drive the anchors into the stomach tissue. In another embodiment, the anchors may be ejected by triggering a releasing spring in the delivery tubes. After the band is secured to the stomach wall, the pusher is pulled proximally to allow the delivery tubes to fold-up away from the band and the stomach wall. The delivery sheath and delivery tubes are then removed from the stomach. Without the force provided by the delivery tubes against the band, the shape-memory band returns to its relaxed unexpanded configuration and draws the attached stomach wall with it, forming a stricture within the stomach cavity to reduce its volume.

Figure 14:
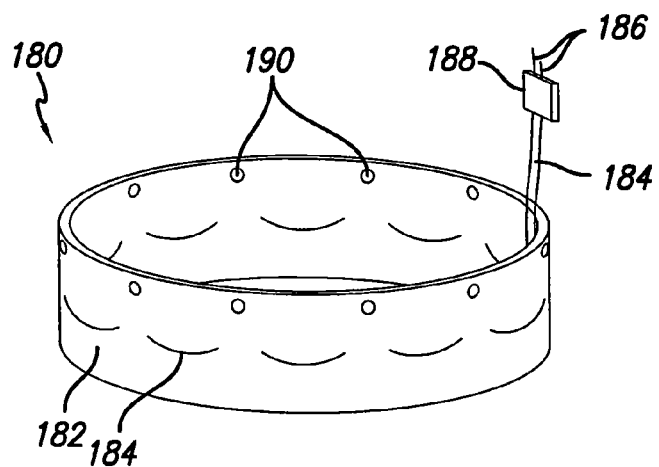
FIG. 14 depicts a perspective view of a fabric intragastric band.

Another embodiment of an intragastric band 180 is shown in FIG. 14. The intragastric band includes a body 182 formed of fabric or mesh material. In alternative embodiments, the body may include elastic material. The fabric/mesh material may include a polyester, PTFE, ePTFE, PET, non-woven, woven, a braided material or mesh, or combination braid or mesh incorporating a fabric and a metal component (produced by Secant Medical, Perkasie, Pa.), etc. This fabric/mesh band includes a tensioning member 184 that is sutured to the band in a purse-string configuration. Two free ends 186 of the tensioning member are joined together with a clip 188 as shown in FIG. 14. The clip is used for adjusting the tension of the tensioning member and maintaining the stricture formed by the band. Fixation points or fenestrations 190 are disposed in the body of the band to allow sutures or anchors to attach the band to the stomach wall. The fixation points may be disposed along the body in any configuration, including a staggered configuration. In use, the fabric/mesh band is attached to the stomach wall, and then the tensioning member is tensioned, thereby cinching and decreasing the diameter of the fabric/mesh band and forming a stricture within the stomach cavity. The clip then locks the free ends of the tensioning member to maintain the stricture. At any time after the initial procedure, the size of the stricture may be adjusted by unlocking the clip and allowing the free ends of the tensioning member to be tightened or loosened.

The tensioning member 184 should be sufficiently flexible to allow for decreasing the diameter of the fabric/mesh band 180. The tensioning member may be formed from a high-tensile, corrosion-resistant material, e.g., Kevlar fiber, braid or cable; stainless steel wire, braid or cable; polypropylene or other suture materials; or nitinol wire, braid, or cable.

Figure 15:
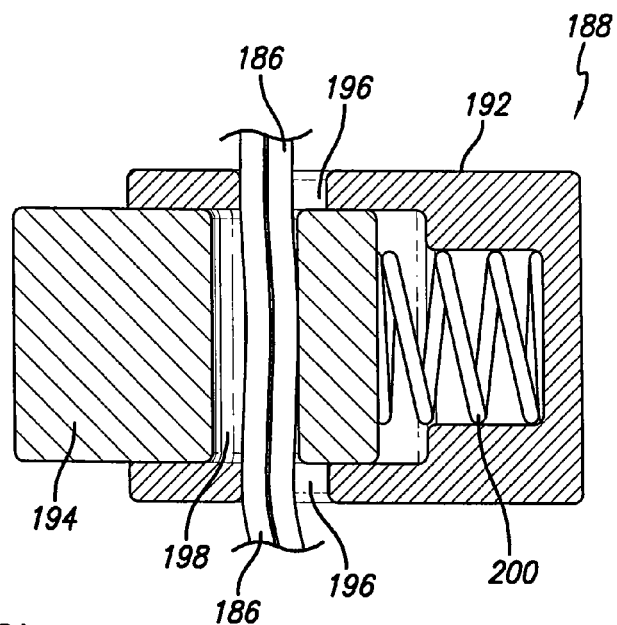
FIG. 15 depicts a cross-sectional view of a clip used to secure a tensioning member.

In one embodiment, the clip 188 is an adjustable clip, as depicted in FIG. 15. Using the adjustable clip, the tensioning member could be adjusted to increase or decrease the tension of the tensioning member at any time without having to re-string a new tensioning member through the fabric/mesh band 180. The adjustable clip includes a housing 192 and a locking member 194 moveable within the housing. A first through-hole 196 is disposed through the housing to accommodate the free ends 186 of the tensioning member 184. The locking member also includes a second through-hole 198, that when lined-up with the first through-hole provides an unrestricted path through the housing and locking member. A spring 200 is disposed within the housing to bias the locking member into a locking position, where the first and second through-holes 153 and 154 are misaligned, thereby locking the free end of the tensioning member within the housing of the adjustable clip. To adjust the tensioning of the tensioning member, the locking member of the adjustable clip is pushed into the housing against the spring force to align the first and second through-holes into an open configuration to allow the tensioning member to move freely through the adjustable clip. Once the tension of the tensioning member has been adjusted, the locking member would be released, and the force of the spring would bias the locking member, thereby misaligning the through-holes and locking the tensioning member in place.

Figure 16:
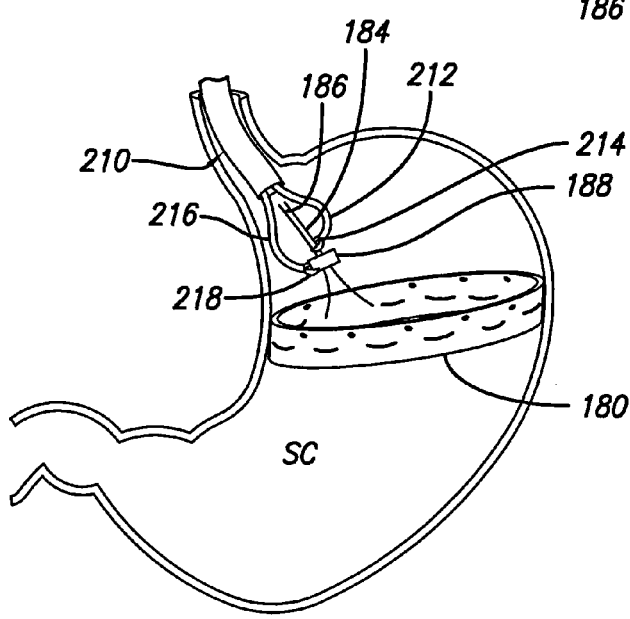
FIG. 16 depicts a schematic view of the fabric intragastric band of FIG. 14 secured within the stomach cavity in an expanded configuration.
Figure 17:
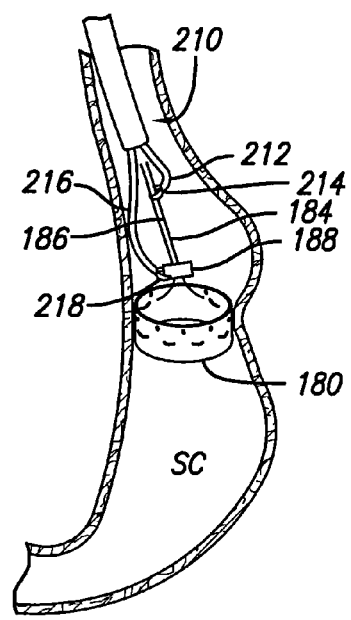
FIG. 17 depicts a schematic view of the stomach cavity of FIG. 16, with the fabric intragastric band tensioned to a reduced diameter and forming a stricture within the stomach cavity.

Referring to FIGS. 16 and 17, a method of tightening the tensioning member 188 of the fabric/mesh band 180 is shown. After the fabric/mesh band has been secured to the stomach wall, a tensioning device 210 can be delivered through the esophagus to the stomach cavity. The tensioning device includes a first grasping device 212 having first graspers 214 that are configured to grasp the free ends 186 of the tensioning member 184. Also, the tensioning device includes a second grasping device 216 having second graspers 218 that are configured to engage the adjustable clip 188 and depress the locking member 194 to allow the tensioning member to be adjusted. Once the desired size of the stricture is obtained, as shown in FIG. 17, the second graspers release the locking member of the clip to lock the position of the tensioning member and maintain the size of the stricture. The tensioning device is removed from the stomach cavity, leaving a stricture that reduces the volume of the stomach cavity.

Figure 18:
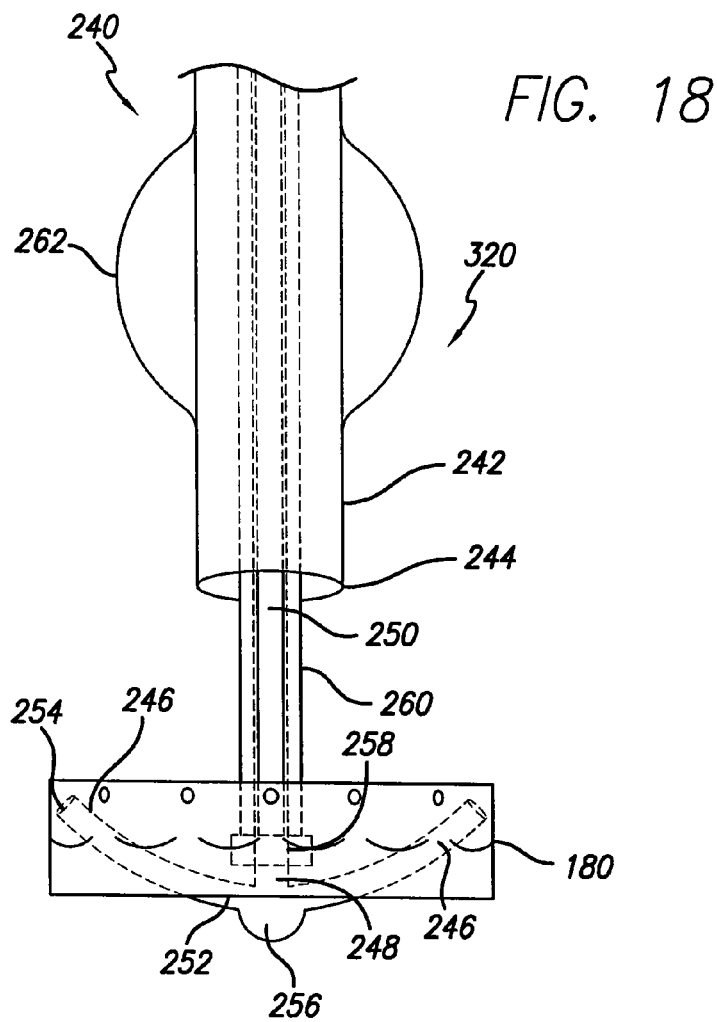
FIG. 18 depicts a partial view of a delivery device used to expand and secure the fabric intragastric band of FIG. 14 to the stomach wall.

Referring now to FIG. 18, a delivery device 240 is shown that can position and secure the fabric/mesh band 180 to the stomach wall. The delivery system includes a delivery sheath 242, which has a distal end 244 and a proximal end (not shown). The delivery sheath houses at least two articulating members or delivery tubes 246 that are flexibly or hingedly attached to a distal end 248 of a central rod 250. The delivery tubes each have an attached end 252 and an ejection end 254. At the distal end of the rod is an atraumatic tip such as a nosecone 256. The system also includes a pusher 258 attached to a hollow tube 260 that is disposed over the central rod. Anchors, such as those described above, may be positioned near the ejection end of the delivery tubes. The fabric/mesh band may also be housed within the delivery sheath. In another embodiment, the fabric/mesh band may be delivered to the stomach cavity in a separate delivery sheath. In one embodiment, an inflatable balloon 262 may be disposed on the outside of the delivery sheath near the distal end. The balloon is positioned and inflated within the esophagus to seal inflow of air to the stomach cavity if use of a vacuum is desired. A vacuum may be used to draw tissue toward or into contact with the delivery system, or in the alternative, positive pressure could be applied to distend the stomach.

In use, the distal end 244 of the delivery system 240 is delivered down the esophagus to the stomach cavity under endoscopic guidance. As the system is delivered, the plurality of delivery tubes 246 are folded inside the delivery sheath 242 with the fabric/mesh band 180. Once in position within the stomach cavity, the delivery sheath is pulled proximally while the central rod 250 is held in position to release the delivery tubes. Next, the pusher 258 is pushed distally until it comes into contact with the attached ends 252 of the delivery tubes to expand the delivery tubes into an expanded configuration as shown in FIG. 18. The fabric/mesh band is positioned on the delivery tubes so that as the delivery tubes expand, the fabric/mesh band is forced into an expanded configuration to come into contact with the stomach wall. To secure the band to the stomach wall, anchors may be ejected from the ejection ends of the delivery tubes, through the fixation points 190 of the band and into the stomach wall. In one embodiment, the anchors are ejected by a pneumatic pressure. In this embodiment, the central rod can provide a pathway to direct air pressure to the delivery tubes to drive the anchors into the stomach tissue. In another embodiment, the anchors may be ejected by triggering a releasing spring in the delivery tubes. Still in another embodiment, sutures may be placed through the fixation points to secure the band to the stomach wall. After the band is secured to the stomach wall, the pusher is pulled proximally to allow the delivery tubes to fold-up away from the band and the stomach wall. The delivery sheath and delivery tubes are then removed from the stomach. The tensioning member is then tensioned, as described above, until a stricture of a desired size is formed in the stomach cavity.

Figure 19:
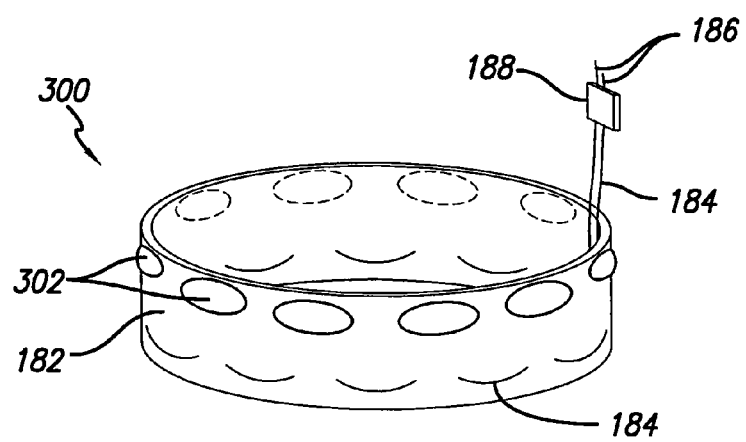
FIG. 19 depicts a perspective view of another embodiment of a fabric intragastric band include adhesive capsules.

Yet another embodiment of an intragastric band 300 is shown in FIG. 19. This embodiment is similar to the intragastric band 180 described above, and therefore like reference numerals will be used to designated like or similar details. The intragastric band 300 includes adhesive capsules 302 attached to the outer surface of the body 182 formed of fabric or mesh material. The adhesive capsules may include any one of the following, cyanoacrylate tissue adhesive such as Cyanoacrylate Ester (Loctite Corporation), UV cure adhesives, adhesive tapes or felts, adhesive foam, or other substrates, including tissue or collagen substrates modified to increase their adherent qualities. The fabric/mesh body of the adhesive band will bond to the stomach wall when the capsules are punctured. To further secure the adhesive band to the stomach wall, sutures may be placed through the fabric/mesh body of the band and into the stomach wall. Once secured to the stomach wall, the size of the adhesive band is reduced in the same manner as described above in relation to the intragastric band 180, by tensioning the tensioning member 184 and securing it with the clip 188.

Figure 20:
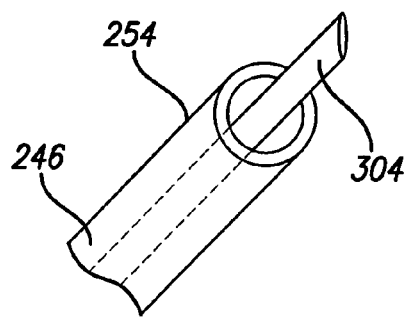
FIG. 20 depicts a partial view of an ejection end of a delivery tube from an embodiment of the delivery device shown in FIG. 18.

Delivery of the adhesive band 300 is also similar to the delivery of the intragastric band 180. The delivery device 240 described above and shown in FIG. 18, could also be used to deliver the adhesive band. However, there would be no need to have anchors housed near the ejection ends 254 of the delivery tubes 246. Instead the delivery tubes would house needles 304 that could be advanced past the ejection end of the delivery tubes to rupture the adhesive capsules 302 disposed on the body 182 of the adhesive band. FIG. 20 depicts an ejection end of the delivery tube with the needle being advanced. After rupturing the adhesive capsules, the needles would be withdrawn into the delivery tubes, and the delivery device would be removed.

Figure 21:
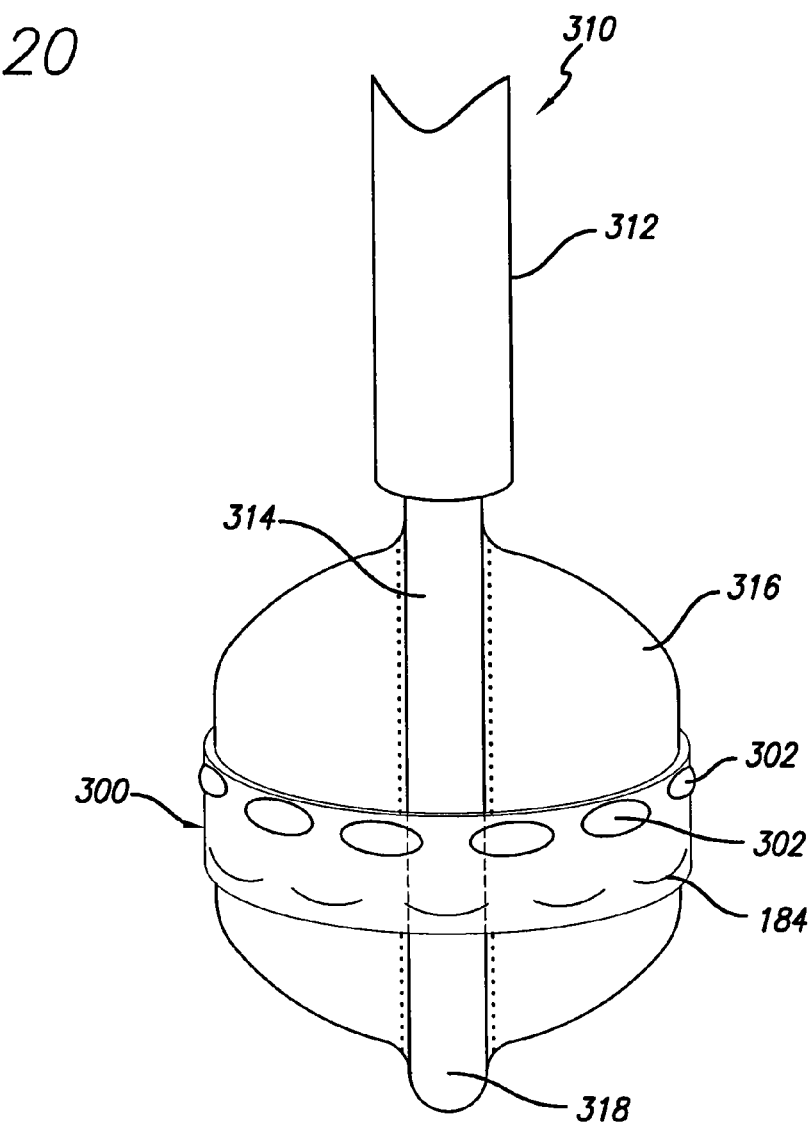
FIG. 21 depicts a partial view of a delivery device used to expand and secure the fabric intragastric band of FIG. 19.

Another embodiment of a delivery device 310 is depicted in FIG. 21, that can be used to deliver the adhesive band 300 to the stomach cavity. The delivery device includes a delivery sheath 312 that houses a delivery catheter 314 with an inflatable balloon 316 attached near a distal end 318 of the catheter. The adhesive band can be housed within the delivery sheath around the deflated balloon. Once the distal end of the delivery device is positioned within the stomach cavity, the delivery sheath can be pulled proximally while the catheter is held in position, exposing the balloon. In another embodiment, the catheter could be delivered through the delivery sheath and out the distal end of the delivery sheath into position within the stomach cavity. In position within the stomach cavity, the balloon is inflated, thereby expanding the adhesive band until it comes into contact with the wall of the stomach. In one embodiment, the balloon is expanded to generate sufficient pressure to rupture the adhesive capsules. After the adhesive band is secured to the stomach wall, the balloon is deflated, and the delivery device is removed from the stomach cavity. The tensioning member 184 of the adhesive band is then tensioned as described above to produce a stricture within the stomach cavity.

Figure 22:
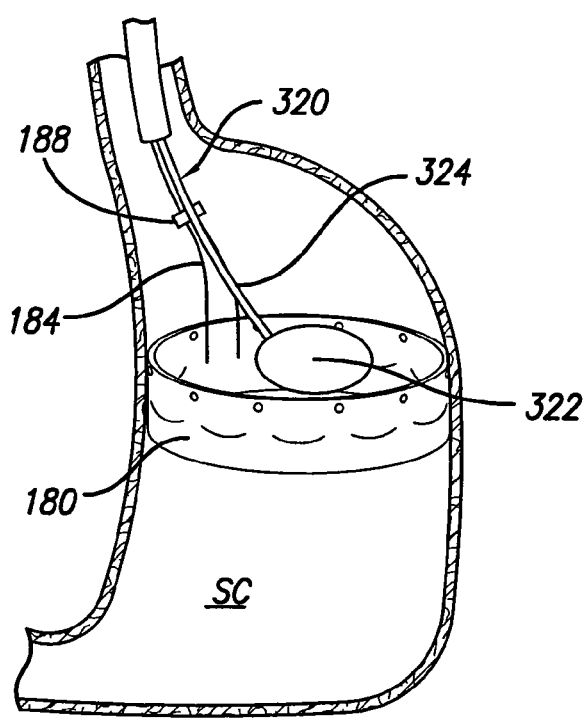
FIG. 22 depicts a schematic view of a balloon inflated in the stomach cavity with the fabric intragastric band secured to the inner stomach wall.
Figure 23:
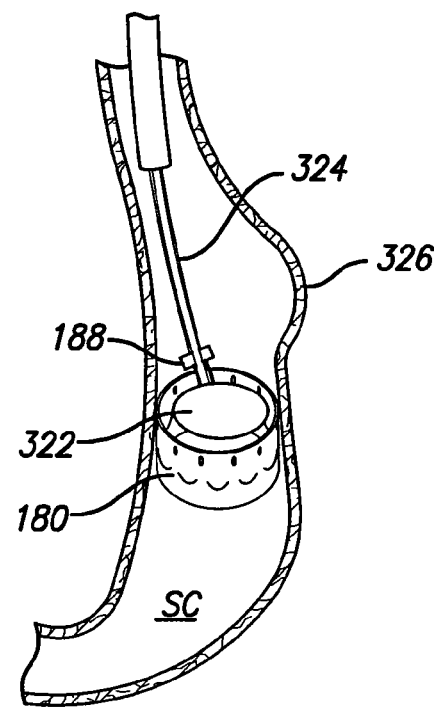
FIG. 23 depicts a schematic view of the fabric intragastric band of FIG. 22 tensioned around the inflated balloon.

As described above, the tensioning member 184 is tensioned or pulled proximally to cinch the fabric/mesh band 180 in order to form the stricture within the stomach cavity SC. In one embodiment, a calibration device 320 may be used to control the cross-sectional area of the stricture. The calibration device includes an inflatable balloon 322 (or other inflatable or expanding device) attached to the distal end of a catheter 324. Once the intragastric band 180 is secured to the stomach wall SW, the calibration device is delivered to the stomach cavity and the balloon is placed in the area of the stomach cavity to be constricted and is inflated to the desired size, as shown in FIG. 22. The calibration device would inherently be adjustable for physician control. The tensioning member is then tensioned until a stricture 326 conforms to the calibration device as shown in FIG. 23. The clip 188 then locks the tensioning member and the balloon is deflated and removed from the stomach cavity. Use of the calibration device is optional and physicians may prefer to control the size of the stricture themselves without the use of the calibration device.

Figure 24:
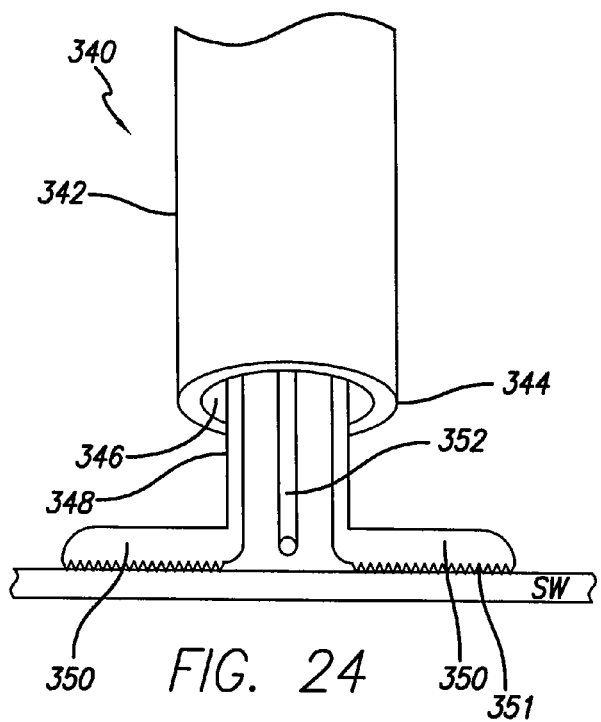
FIGS. 24 through 26 depict partial views of a delivery system used to apply create and secure folds of stomach tissue together with an adhesive.
Figure 25:
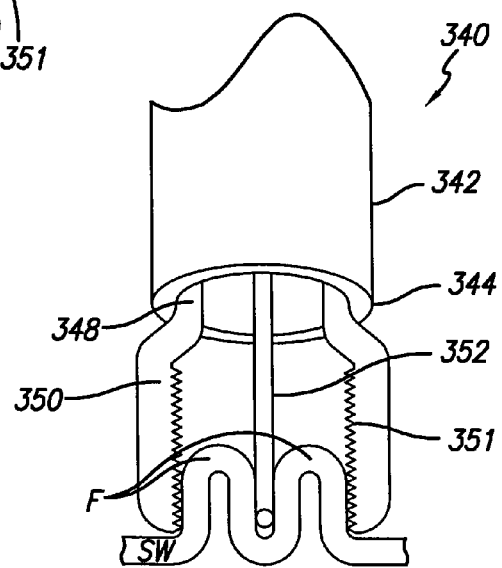
Figure 26:
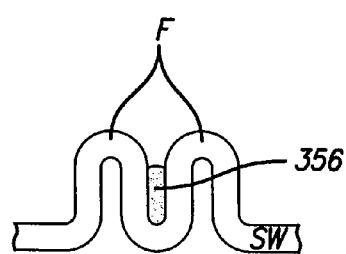

Another embodiment of a method for reducing the volume of the stomach cavity includes creating and securing folds of stomach tissue together. In another embodiment, the intragastric bands described above could be attached to the folds created within the stomach cavity. FIGS. 24 through 26 depict one embodiment of a device used to create folds within the stomach cavity using an adhesive. Referring to FIG. 24, a delivery system 340 includes a delivery sheath 342 having a proximal end (not shown) and a distal end 344, with a central lumen 346 disposed at least partially between the proximal and distal ends. A delivery tube 348 is housed within the central lumen, and the delivery tube includes jaws 350 that move from an open configuration to a closed configuration. The jaws may include a textured surface 351 to better grasp the stomach tissue without slipping. There is also a dispensing tube 352 located within a lumen of the delivery tube. The dispensing tube helps create folds and then dispenses adhesive to secure the folds together. In use, the delivery sheath is placed within the stomach and the delivery tube is moved distally out of the delivery sheath, and the jaws of the delivery tube are moved to an open configuration as shown in FIG. 24. The dispensing tube is then advanced until its distal tip 354 comes into contact with the stomach wall SW. With the distal tip of the dispensing tube against the stomach wall, the jaws of the delivery tube are moved into a closed configuration as shown in FIG. 25. As the jaws move to the closed configuration, the textured surfaces grip the stomach wall, thereby forming a dual fold F around the dispensing tube. Adhesive 356 is then dispensed from the distal tip of the dispensing tube filling the gap between the dual folds, and eventually bonding the dual folds together, as shown in FIG. 26. The delivery system could then be repositioned within the stomach cavity to create any number of dual folds within the stomach cavity. After which, the dispensing tube and delivery tube along with its jaws are retracted into the delivery sheath and removed from the stomach cavity. Forming any number of folds along the stomach wall will reduce the volume of the stomach cavity.

Figure 27:
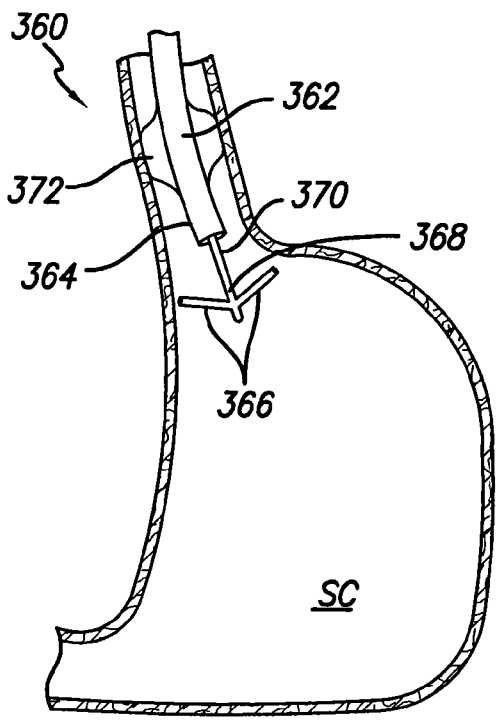
FIGS. 27 and 28 depict a schematic view of a delivery system that can create multiple folds simultaneously within the stomach cavity.

FIG. 27 depicts a schematic view of a delivery system 360 that can create multiple folds simultaneously within the stomach cavity. The delivery system includes a delivery sheath 362, which has a distal end 364 and a proximal end (not shown). The delivery sheath houses at least two articulating members or delivery tubes 366 that are flexibly or hingedly attached to a distal end 368 of a central rod 370. In one embodiment, an inflatable balloon 372 may be disposed on the outside of the delivery sheath near the distal end. The balloon is positioned and inflated within the esophagus to seal inflow of air to the stomach cavity if use of a vacuum is desired. A vacuum may be used to draw tissue toward or into contact with the delivery system, or in the alternative, positive pressure could be applied to distend the stomach.

Figure 28:
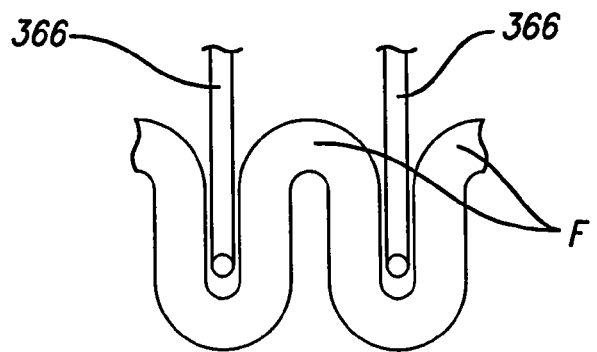

During the procedure, the distal end 364 of the delivery system 360 is delivered down the esophagus to the stomach cavity under endoscopic guidance. As the system is delivered, the plurality of delivery tubes 366 are folded inside the delivery sheath 362. Once in position within the stomach cavity, the delivery sheath is pulled proximally while the central rod 370 is held in position to release the delivery tubes. In one embodiment, a pusher is pushed distally until it expands the delivery tubes into an expanded configuration as shown in FIG. 27. In another embodiment, the delivery tubes self expand into the expanded configuration. The balloon may be expanded in the esophagus to provide support and a seal for when a vacuum is applied to the stomach cavity. A vacuum source may be connected to a lumen of the delivery sheath to create a vacuum within the stomach cavity, drawing tissue into contact with the delivery tubes and creating folds as shown in FIG. 28. Adhesive is then dispensed from the delivery tubes to bond the folds F together. After the folds are secured, the vacuum may be stopped and the delivery system is removed from the stomach cavity.

The plurality of folds created with the delivery systems 340 or 360, can then be connected together to form a stricture within the stomach cavity. In one embodiment the intragastric bands described above can be delivered to the stomach cavity and attached to the folds, using adhesive, sutures, anchors, or a combination of adhesive, sutures and anchors. Once attached to the folds, the band can be cinched, as described above, to reduce the volume of the stomach. The folds may also be connected together with a tensioning member, suture, clips, anchors, staples, or other devices as well to further reduce the volume of the stomach cavity.

Intragastric bands could also be incorporated into a fold created by a certain device. One device that could be used to place the anchors discussed above in the stomach wall is disclosed in U.S. Ser. No. 10/797,439 ("the '439 application"), titled "Devices And Methods For Placement Of Partitions Within A Hollow Body Organ." The '439 application is hereby incorporated by reference in its entirety. The tissue acquisition and fixation device disclosed in the '439 application is used to create longitudinal dual fold plications within the stomach wall. Slightly altered, the tissue acquisition and fixation device could be used to fix the intragastric bands, specifically the fabric/mesh bands, into the dual fold plications. After being fixed within the dual fold, the fabric/mesh band would be tightened using the tensioning member as described above to form a stricture within the stomach cavity. Fixing the intragastric band within dual folds could facilitate a secure connection that is less likely to deteriorate for various reasons, including that the plications distribute the load the stomach tissue acquires when it is brought together to narrow the organ which aids healing. Also, the fixation device may be designed to incorporate at least two layers of stomach wall tissue, and sometimes additional layers including the serosal layer, can provide greater healing durability once the tissues are in tension in the organ's reduced state.

Figure 29:
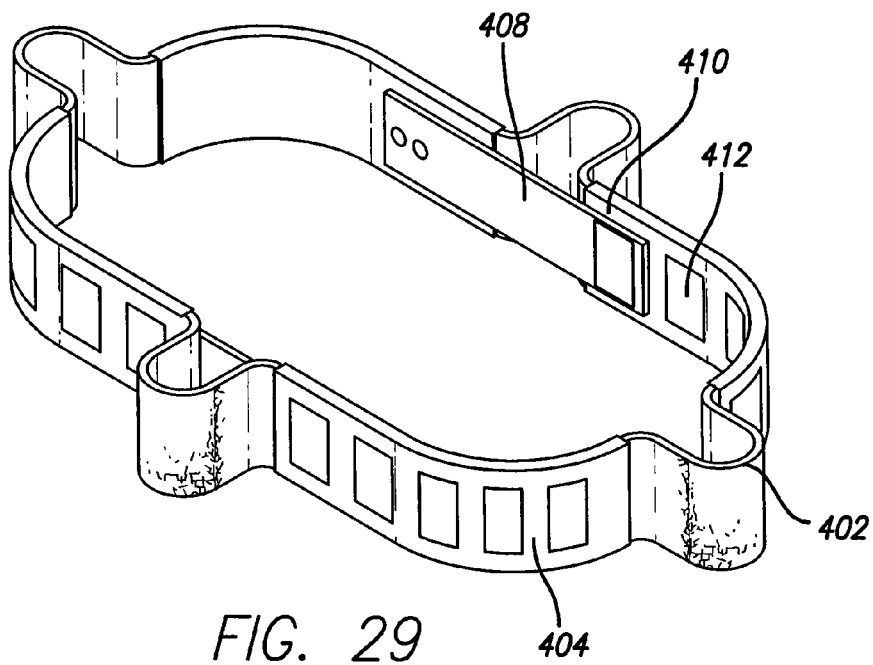
FIG. 29 depicts a perspective view of another embodiment of an intragastric band.
Figure 30:
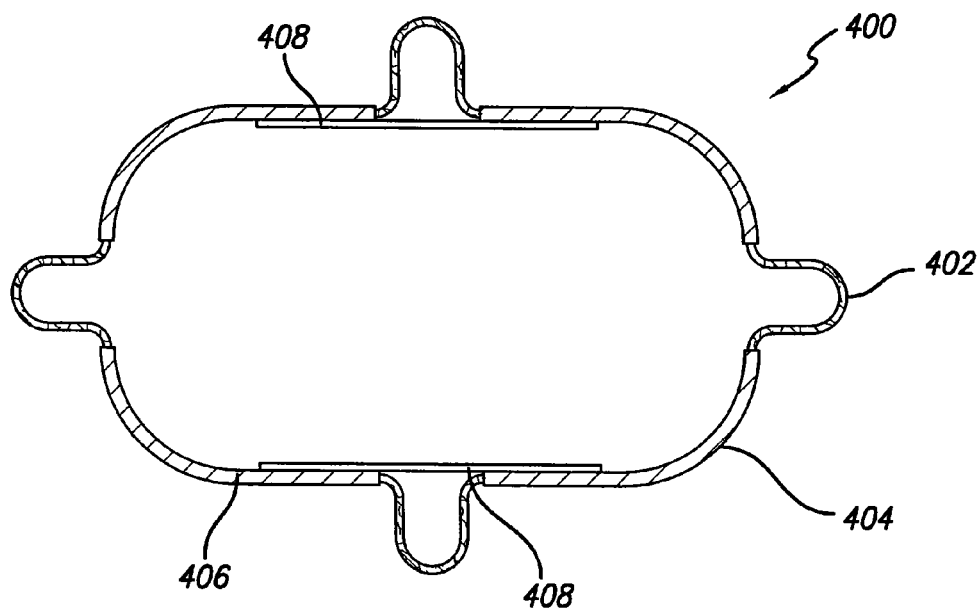
FIG. 30 depicts a top planar view of the intragastric band of FIG. 29.

Another embodiment of an intragastric band 400 is shown in FIGS. 29 and 30, and can also be incorporated into a dual fold created by the tissue acquisition and fixation device disclosed in the '439 application. The intragastric band 400 includes flexible sections 402 and more resilient sections 404 alternating with one another around the body 406 of the band. In one embodiment, there are four flexible sections and four more resilient sections, however, the band could include two or more flexible and more resilient sections. The more flexible regions may be as frequent as ten or higher to maximize the apposition of the band to the surrounding tissue. The flexible section can include fabric or mesh, and may even include an elastic material. The more resilient section can include a hard polymer or a metal such as stainless steel, or a less hard, more conformable material such as silicone to assist in apposition of the band and prevent leaks in the non-anchored regions of the band. In an embodiment where an adjustable band is desired, an optional ratchet mechanism 408 is attached to the more resilient sections including an attachment end 410 that locks into size-adjustment steps 412 disposed in the more resilient sections. The embodiment shown includes two ratchet mechanisms, although the number of ratchet mechanisms could be equal to the number of more resilient sections. After the band is secured to the stomach cavity, the attachment end of the ratchet mechanism can be locked into the desired size-adjustment step to provide the desired diameter of the intragastric band and the stricture. The ratchet mechanism could also be similar to the adjustment mechanism 32 described with the intragastric band 20 shown in FIG. 1. Because the flexible sections are incorporated into the tissue folds upon placement of the band, the adjustable feature of the present invention may not be required in all cases. Similarly, it may be desirable to size the band prior to implantation, thereby simplifying the procedure and not requiring a secondary adjustment step.

Figure 31:
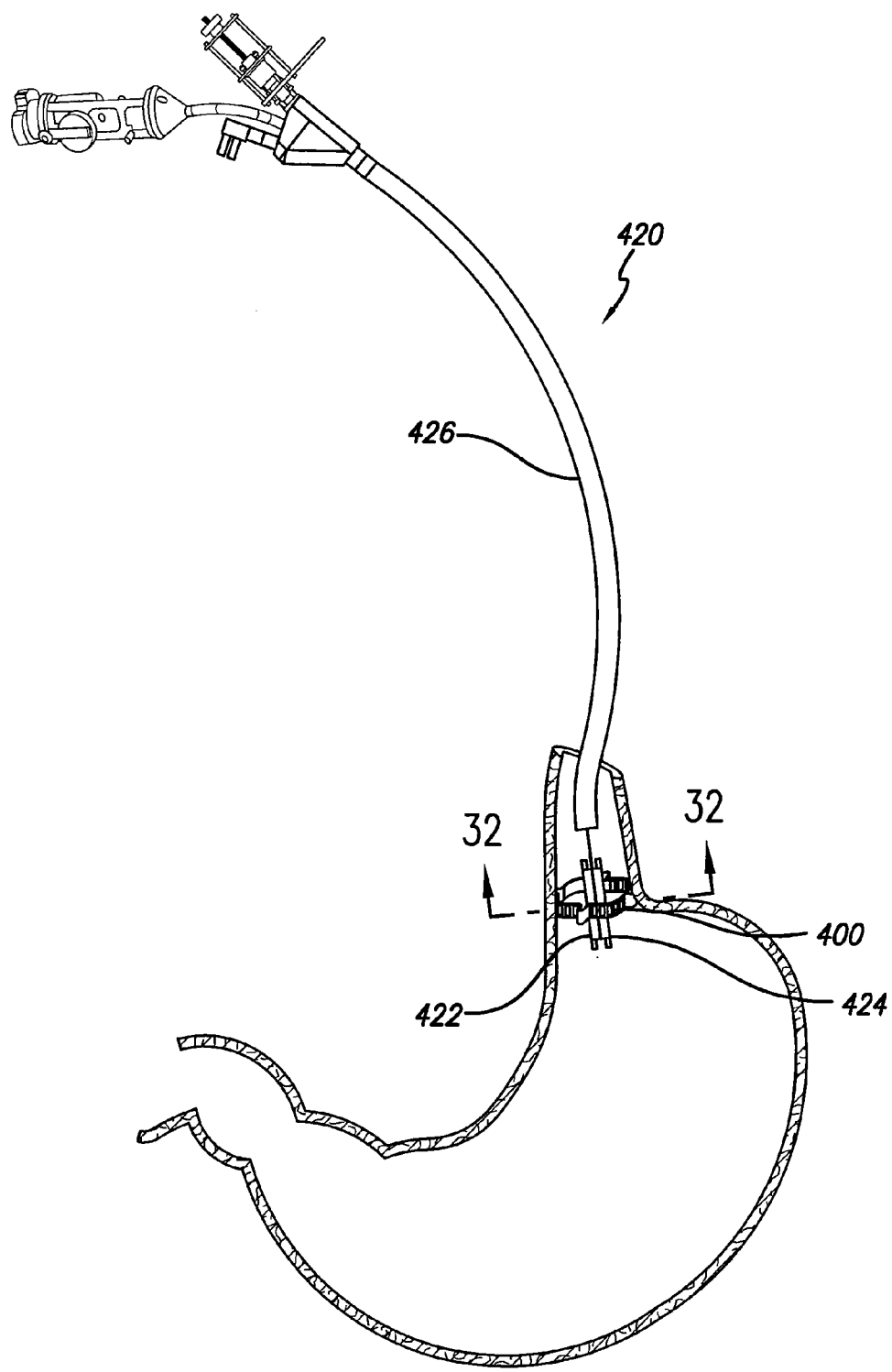
FIG. 31 depicts a schematic view of a tissue acquisition and fixation device used to incorporate a portion of the intragastric band of FIG. 29 into a plication formed along the stomach wall.
Figure 32:
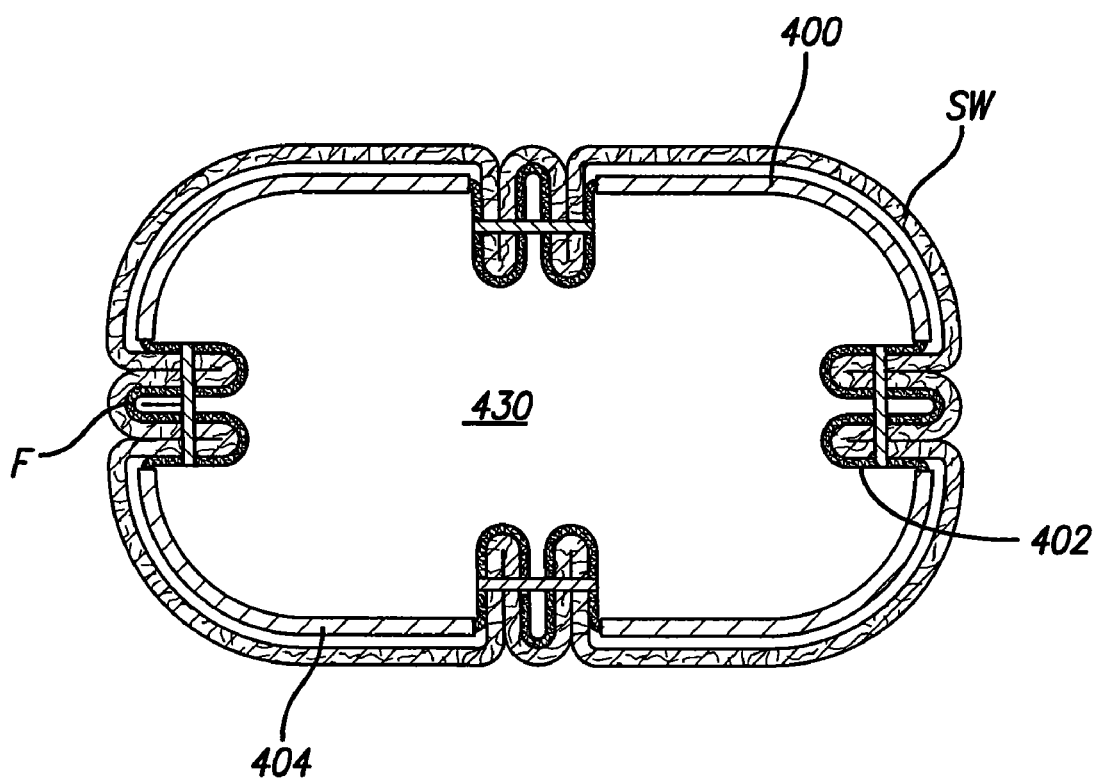
FIG. 32 depicts a cross-sectional view taken along line 32-32 of FIG. 31.

In one embodiment of a method for securing the intragastric band 400 to the stomach wall is shown in FIGS. 31 and 32. The intragastric band can first be secured to the stomach wall using adhesive, sutures, or anchors. The delivery device 240 as described above could be used to first secure the intragastric band to the stomach wall. After which, the tissue acquisition and fixation device is delivered to the stomach as shown in FIG. 29. The tissue acquisition and fixation device 420 includes a cartridge member 422 and an anvil member 424 that are connected to a tubular member and housed within a delivery sheath 426. Cartridge member may contain one or more anchors, such as a cartridge of staples, which may be actuated via controls located proximally at a handle assembly. A septum or barrier (not shown) may be removably positioned between the cartridge member and the anvil member. Also, both the cartridge and anvil members may include vacuum openings that are used to acquire tissue. Applying a vacuum to the vacuum openings acquires tissue and the septum forms a barrier to create a dual fold. If a septum is used, it must be removed before the cartridge and anvil members are actuated to place the staple line within the dual fold. The cartridge and anvil members of the tissue acquisition and fixation device are positioned near one of the flexible sections 402 of the band 400, and then the vacuum is created to draw the tissue and the flexible section of the band into the vacuum openings. The tissue acquisition and fixation device is then actuated to place a line of staples into the flexible section and stomach tissue, forming a plication. This is repeated for the remaining flexible sections, thereby providing a durable connection between the band and the stomach wall. The optional ratchet mechanism may then be adjusted to set the desired size of the stricture within the stomach cavity. In another placement technique of the present invention, the band is sheathed or held directly onto the tissue acquisition and fixation device 420, and both are placed together into the fixation region. In this initial placement, it would be desirable for the flexible region and the tissue acquisition opening to be aligned for initial placement, after which time the tissue acquisition and fixation device may be rotated to the next flexible region and activated to fix the next flexible region to adjacent tissue.

FIG. 32 shows a cross-section view taken along line 32-32 of FIG. 31. The flexible sections 402 of the intragastric band 400 are shown to be fixed into the dual folds F created by the tissue acquisition and fixation device 420. The stricture or stoma 430 formed by the intragastric band may optionally be adjusted to any desirable size using the ratchet mechanism or sized prior to implantation. Although the intragastric band 400 was discussed in this embodiment, the fabric/mesh band and the adhesive band could also be used with the tissue acquisition and fixation device. For example, with the fabric/mesh band, the tissue acquisition and fixation device could fix any location along flexible body 182 of the fabric/mesh band into dual folds of stomach tissue. It would be preferred that the sections of the flexible body that are incorporated into the dual folds be located equally along the body. To adjust the size of the stricture or stoma formed, the tensioning member 184 could still be tensioned through the plications and locked with the clip 188 as described above.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While the dimensions, types of materials described herein are intended to define the parameters of the invention, they are by no means limiting and are exemplary embodiments.

I claim:

1. A system for reducing a volume of a stomach cavity, comprising:
    a band having a plurality of segments with a radially inwardly facing surface, a radially outwardly facing surface, and top and bottom edges, and a plurality of radially outwardly projecting flexible belts connecting the segments where the belts form tissue folds attachment positions on the band;
    wherein the band creates a stricture to reduce the volume within the stomach cavity when attached to a wall of the stomach cavity and contracted to a reduced diameter.

2. The system of claim 1 further comprising an adjustment mechanism located on a radially inwardly facing surface of a segment of the band for changing the diameter of the band.

3. The system of claim 2 further comprising an acquisition and fixation device having a cartridge and anvil connected to a tubular member for creating a dual fold of stomach tissue and fixing the dual fold of stomach tissue to the belt of the band.

4. The system of claim 3 further comprising vacuum ports on the acquisition and fixation device for drawing stomach tissue to create the dual folds of stomach tissue.

5. The system of claim 4 further comprising a removable septum disposed between the vacuum ports.

6. The system of claim 3 wherein the cartridge comprises a plurality of staples.

7. The system of claim 3 wherein the band is coupled directly to the acquisition and fixation device during delivery of the band.

8. The system of claim 3 wherein the band is sheathed on the acquisition and fixation device during delivery of the band.

* * * * *